(12) United States Patent
Babkes et al.

(10) Patent No.: US 9,498,365 B2
(45) Date of Patent: Nov. 22, 2016

(54) INTRAGASTRIC IMPLANTS WITH MULTIPLE FLUID CHAMBERS

(75) Inventors: Mitchell H. Babkes, Santa Clarita, CA (US); Zachary Dominguez, Santa Barbara, CA (US); Christopher S. Mudd, Ventura, CA (US); Craig Olroyd, Santa Barbara, CA (US); Jonathan Daugusta, Corona del Mar, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 273 days.

(21) Appl. No.: 13/275,224

(22) Filed: Oct. 17, 2011

(65) Prior Publication Data

US 2012/0191125 A1    Jul. 26, 2012

Related U.S. Application Data

(60) Provisional application No. 61/478,013, filed on Apr. 21, 2011, provisional application No. 61/394,685, filed on Oct. 19, 2010, provisional application No. 61/394,592, filed on Oct. 19, 2010.

(51) Int. Cl.
*A61M 29/00* (2006.01)
*A61F 5/00* (2006.01)

(52) U.S. Cl.
CPC ........... *A61F 5/0033* (2013.01); *A61F 5/0036* (2013.01)

(58) Field of Classification Search
CPC .............................. A61F 5/0003; A61F 5/0036
USPC ................ 606/191, 198; 604/909; 623/23.65
See application file for complete search history.

(56) References Cited

U.S. PATENT DOCUMENTS

| | | |
|---|---|---|
| 1,702,974 A | 2/1929 | MacDonald |
| 2,087,604 A | 7/1937 | Mosher |
| 2,163,048 A | 6/1939 | McKee |
| 2,619,138 A | 11/1952 | Marler |
| 3,667,081 A | 6/1972 | Burger |
| 3,719,973 A | 3/1973 | Bell |
| 3,840,018 A | 10/1974 | Heifetz |

(Continued)

FOREIGN PATENT DOCUMENTS

| | | |
|---|---|---|
| CN | 1250382 A | 4/2000 |
| CN | 1367670 A | 9/2002 |

(Continued)

OTHER PUBLICATIONS

Xanthakos et al.; 'Bariatric Surgery for Extreme Adolescent Obesity: Indications, Outcomes, and Physiologic Effects on the Gut-Brain Axis'; Pathophysiology; V. 15; pp. 135-146; 2008.

(Continued)

*Primary Examiner* — Richard Louis
(74) *Attorney, Agent, or Firm* — Gordon & Jacobson, P.C.

(57) ABSTRACT

An intragastric obesity treatment implant promotes a feeling of satiety in the patient by contacting the insides of the stomach wall, reducing the space in the stomach, or otherwise reducing the amount of food consumed. One intragastric obesity treatment implant two inflatable balloons coupled via a flow restrictor through which fluid may flow in response to peristaltic motions of a patient's stomach. Additionally, one implant comprises a pumping chamber coupled to a reservoir, where the pumping chamber moves stomach fluids into the reservoir in response to peristaltic motions of the patient's stomach.

16 Claims, 20 Drawing Sheets

(56) References Cited

U.S. PATENT DOCUMENTS

| | | | |
|---|---|---|---|
| 3,919,724 A | 11/1975 | Sanders | |
| 4,118,805 A | 10/1978 | Reimels | |
| 4,364,379 A * | 12/1982 | Finney | 600/40 |
| 4,416,267 A | 11/1983 | Garren et al. | |
| 4,430,392 A | 2/1984 | Kelley | |
| 4,485,805 A | 12/1984 | Foster | |
| 4,545,367 A | 10/1985 | Tucci | |
| 4,586,501 A | 5/1986 | Claracq | |
| 4,592,355 A | 6/1986 | Antebi | |
| 4,598,699 A | 7/1986 | Garren | |
| 4,607,618 A | 8/1986 | Angelchik | |
| 4,636,213 A | 1/1987 | Pakiam | |
| 4,648,383 A | 3/1987 | Angelchik | |
| 4,694,827 A | 9/1987 | Weiner | |
| 4,723,547 A | 2/1988 | Kullas | |
| 4,739,758 A | 4/1988 | Lai et al. | |
| 4,773,432 A | 9/1988 | Rydell | |
| 4,774,956 A | 10/1988 | Kruse et al. | |
| 4,844,068 A | 7/1989 | Arata et al. | |
| 4,881,939 A | 11/1989 | Newman | |
| 4,899,747 A | 2/1990 | Garren et al. | |
| 4,925,446 A | 5/1990 | Garay et al. | |
| 4,930,535 A | 6/1990 | Rinehold | |
| 4,950,258 A | 8/1990 | Kawai | |
| 4,969,899 A | 11/1990 | Cox | |
| 5,074,868 A | 12/1991 | Kuzmak | |
| 5,084,061 A | 1/1992 | Gau | |
| 5,211,371 A | 5/1993 | Coffee | |
| 5,226,429 A | 7/1993 | Kuzmak | |
| 5,242,398 A * | 9/1993 | Knoll et al. | 604/103.05 |
| 5,255,690 A | 10/1993 | Keith | |
| 5,259,399 A | 11/1993 | Brown | |
| 5,289,817 A | 3/1994 | Williams | |
| 5,308,324 A | 5/1994 | Hammerslag | |
| 5,312,343 A | 5/1994 | Krog et al. | |
| 5,449,368 A | 9/1995 | Kuzmak | |
| 5,514,176 A | 5/1996 | Bosley | |
| 5,527,340 A | 6/1996 | Vogel | |
| 5,540,701 A | 7/1996 | Sharkey | |
| 5,547,458 A | 8/1996 | Ortiz | |
| 5,601,604 A | 2/1997 | Vincent | |
| 5,658,298 A | 8/1997 | Vincent | |
| 5,693,014 A | 12/1997 | Abele | |
| 5,725,507 A | 3/1998 | Petrick | |
| 5,748,200 A | 5/1998 | Funahashi | |
| 5,776,160 A | 7/1998 | Pasricha | |
| 5,819,749 A | 10/1998 | Lee | |
| 5,820,584 A | 10/1998 | Crabb | |
| RE36,176 E | 3/1999 | Kuzmak | |
| 5,938,669 A | 8/1999 | Klaiber | |
| 6,074,341 A | 6/2000 | Anderson | |
| 6,102,678 A | 8/2000 | Peclat | |
| 6,102,897 A | 8/2000 | Lang | |
| 6,102,922 A | 8/2000 | Jakobsson | |
| 6,152,922 A | 11/2000 | Ouchi | |
| 6,183,492 B1 | 2/2001 | Hart | |
| 6,264,700 B1 | 7/2001 | Kilcoyne et al. | |
| 6,290,575 B1 | 9/2001 | Shipp | |
| 6,322,538 B1 | 11/2001 | Elbert et al. | |
| 6,450,946 B1 | 9/2002 | Forsell | |
| 6,454,699 B1 | 9/2002 | Forsell | |
| 6,454,785 B2 | 9/2002 | De Hoyos Garza | |
| 6,464,628 B1 | 10/2002 | Forsell | |
| 6,470,892 B1 | 10/2002 | Forsell | |
| 6,503,264 B1 | 1/2003 | Birk | |
| 6,511,490 B2 | 1/2003 | Robert | |
| 6,540,789 B1 | 4/2003 | Silverman et al. | |
| 6,547,801 B1 | 4/2003 | Dargent | |
| 6,579,301 B1 | 6/2003 | Bales et al. | |
| 6,629,776 B2 | 10/2003 | Bell | |
| 6,675,809 B2 | 1/2004 | Stack et al. | |
| 6,682,473 B1 | 1/2004 | Matsuura | |
| 6,733,512 B2 | 5/2004 | McGhan | |
| 6,733,513 B2 | 5/2004 | Boyle | |
| 6,746,460 B2 | 6/2004 | Gannoe | |
| 6,776,783 B1 | 8/2004 | Frantzen | |
| 6,840,257 B2 | 1/2005 | Dario | |
| 6,845,776 B2 | 1/2005 | Stack et al. | |
| 6,905,471 B2 | 6/2005 | Leivseth | |
| 6,960,233 B1 | 11/2005 | Berg | |
| 6,981,978 B2 | 1/2006 | Gannoe | |
| 6,981,980 B2 | 1/2006 | Sampson et al. | |
| 6,994,095 B2 | 2/2006 | Burnett | |
| 7,008,419 B2 | 3/2006 | Shadduck | |
| 7,020,531 B1 | 3/2006 | Colliou | |
| 7,033,384 B2 | 4/2006 | Gannoe et al. | |
| 7,037,344 B2 | 5/2006 | Kagan et al. | |
| 7,056,305 B2 | 6/2006 | Garza Alvarez | |
| 7,090,699 B2 | 8/2006 | Geitz | |
| 7,214,233 B2 | 5/2007 | Gannoe et al. | |
| 7,220,237 B2 | 5/2007 | Gannoe et al. | |
| 7,220,284 B2 | 5/2007 | Kagan et al. | |
| 7,223,277 B2 | 5/2007 | DeLegge | |
| 7,320,696 B2 | 1/2008 | Gazi et al. | |
| 7,347,875 B2 | 3/2008 | Levine et al. | |
| 7,354,454 B2 | 4/2008 | Stack et al. | |
| 7,476,256 B2 | 1/2009 | Meade et al. | |
| 7,510,559 B2 | 3/2009 | Deem et al. | |
| 7,608,114 B2 | 10/2009 | Levine et al. | |
| 7,628,442 B1 | 12/2009 | Spencer | |
| 7,682,330 B2 | 3/2010 | Meade et al. | |
| 7,695,446 B2 | 4/2010 | Levine et al. | |
| 7,699,863 B2 | 4/2010 | Marco et al. | |
| 7,753,870 B2 | 7/2010 | Demarais et al. | |
| 7,771,382 B2 | 8/2010 | Levine et al. | |
| 7,794,447 B2 | 9/2010 | Dann et al. | |
| 7,815,589 B2 | 10/2010 | Meade et al. | |
| 7,837,643 B2 | 11/2010 | Levine et al. | |
| 7,841,503 B2 | 11/2010 | Sonnenschein et al. | |
| 7,883,525 B2 | 2/2011 | DeLegge | |
| 7,931,693 B2 | 4/2011 | Binmoeller | |
| 7,981,162 B2 | 7/2011 | Stack et al. | |
| 8,029,455 B2 | 10/2011 | Stack et al. | |
| 8,032,223 B2 | 10/2011 | Imran | |
| 8,075,582 B2 | 12/2011 | Lointier | |
| 8,162,969 B2 | 4/2012 | Brister | |
| 8,187,297 B2 | 5/2012 | Makower | |
| 8,216,266 B2 | 7/2012 | Hively | |
| 2002/0019577 A1 | 2/2002 | Arabia | |
| 2002/0055757 A1 | 5/2002 | Torre | |
| 2002/0095181 A1 | 7/2002 | Beyar | |
| 2002/0139208 A1 | 10/2002 | Yatskov | |
| 2002/0183782 A1 | 12/2002 | Tsugita | |
| 2003/0045896 A1 | 3/2003 | Murphy | |
| 2003/0073880 A1 | 4/2003 | Polsky | |
| 2003/0074054 A1 | 4/2003 | Duerig | |
| 2003/0100822 A1 | 5/2003 | Lew | |
| 2003/0106761 A1 | 6/2003 | Taylor | |
| 2003/0109935 A1 | 6/2003 | Geitz | |
| 2003/0144575 A1 | 7/2003 | Forsell | |
| 2003/0153905 A1 | 8/2003 | Edwards et al. | |
| 2003/0158570 A1 | 8/2003 | Ferrazzi | |
| 2004/0044357 A1 | 3/2004 | Gannoe et al. | |
| 2004/0092892 A1 | 5/2004 | Kagan et al. | |
| 2004/0117031 A1 | 6/2004 | Stack et al. | |
| 2004/0122452 A1 | 6/2004 | Deem et al. | |
| 2004/0122453 A1 | 6/2004 | Deem et al. | |
| 2004/0143342 A1 | 7/2004 | Stack et al. | |
| 2004/0148034 A1 | 7/2004 | Kagan | |
| 2004/0172142 A1 | 9/2004 | Stack | |
| 2004/0186503 A1 | 9/2004 | DeLegge | |
| 2005/0033332 A1 | 2/2005 | Burnett | |
| 2005/0049718 A1 | 3/2005 | Dann et al. | |
| 2005/0055039 A1 | 3/2005 | Burnett et al. | |
| 2005/0085923 A1 | 4/2005 | Levine et al. | |
| 2005/0096692 A1 | 5/2005 | Linder et al. | |
| 2005/0131485 A1 | 6/2005 | Knudson | |
| 2005/0190070 A1 | 9/2005 | Rudduck | |
| 2005/0192614 A1 | 9/2005 | Binmoeller | |
| 2005/0192615 A1 | 9/2005 | Torre | |
| 2005/0197714 A1 | 9/2005 | Sayet | |
| 2005/0228504 A1 | 10/2005 | Demarais | |
| 2005/0240279 A1 | 10/2005 | Kagan | |
| 2005/0250979 A1 | 11/2005 | Coe | |

(56) References Cited

U.S. PATENT DOCUMENTS

| | | |
|---|---|---|
| 2005/0256533 A1 | 11/2005 | Roth |
| 2005/0261711 A1 | 11/2005 | Okada |
| 2005/0267595 A1 | 12/2005 | Chen et al. |
| 2005/0267596 A1 | 12/2005 | Chen et al. |
| 2005/0273060 A1* | 12/2005 | Levy et al. .................. 604/192 |
| 2005/0277975 A1 | 12/2005 | Saadat |
| 2006/0020278 A1 | 1/2006 | Burnett |
| 2006/0025799 A1 | 2/2006 | Basu |
| 2006/0069403 A1 | 3/2006 | Shalon |
| 2006/0106288 A1 | 5/2006 | Roth |
| 2006/0142700 A1 | 6/2006 | Sobelman |
| 2006/0178691 A1 | 8/2006 | Binmoeller |
| 2006/0190019 A1 | 8/2006 | Gannoe |
| 2006/0217762 A1 | 9/2006 | Maahs |
| 2006/0229702 A1 | 10/2006 | Agnew |
| 2006/0252983 A1 | 11/2006 | Lembo et al. |
| 2007/0010864 A1 | 1/2007 | Dann et al. |
| 2007/0016262 A1 | 1/2007 | Gross et al. |
| 2007/0021761 A1 | 1/2007 | Phillips |
| 2007/0078476 A1 | 4/2007 | Hull, Sr. et al. |
| 2007/0083224 A1* | 4/2007 | Hively .......................... 606/192 |
| 2007/0100368 A1 | 5/2007 | Quijano et al. |
| 2007/0118168 A1 | 5/2007 | Lointier et al. |
| 2007/0135803 A1 | 6/2007 | Belson |
| 2007/0135829 A1 | 6/2007 | Paganon |
| 2007/0147170 A1 | 6/2007 | Hood |
| 2007/0149994 A1 | 6/2007 | Sosnowski |
| 2007/0156013 A1 | 7/2007 | Birk |
| 2007/0156248 A1 | 7/2007 | Marco |
| 2007/0173881 A1 | 7/2007 | Birk et al. |
| 2007/0185374 A1 | 8/2007 | Kick |
| 2007/0185375 A1 | 8/2007 | Stad et al. |
| 2007/0239284 A1 | 10/2007 | Skerven et al. |
| 2007/0250020 A1 | 10/2007 | Kim |
| 2007/0265598 A1 | 11/2007 | Karasik |
| 2007/0276428 A1 | 11/2007 | Haller |
| 2007/0288033 A1 | 12/2007 | Murature |
| 2007/0293716 A1 | 12/2007 | Baker et al. |
| 2008/0015618 A1 | 1/2008 | Sonnenschein et al. |
| 2008/0058840 A1 | 3/2008 | Albrecht et al. |
| 2008/0058887 A1 | 3/2008 | Griffin et al. |
| 2008/0065122 A1 | 3/2008 | Stack |
| 2008/0071305 A1 | 3/2008 | DeLegge |
| 2008/0097513 A1 | 4/2008 | Kaji et al. |
| 2008/0167606 A1 | 7/2008 | Dann |
| 2008/0172079 A1 | 7/2008 | Birk |
| 2008/0208240 A1 | 8/2008 | Paz |
| 2008/0208241 A1 | 8/2008 | Weiner et al. |
| 2008/0221595 A1 | 9/2008 | Surti |
| 2008/0228205 A1 | 9/2008 | Sharkey |
| 2008/0234718 A1 | 9/2008 | Paganon et al. |
| 2008/0234834 A1 | 9/2008 | Meade et al. |
| 2008/0243071 A1 | 10/2008 | Quijano |
| 2008/0243166 A1 | 10/2008 | Paganon et al. |
| 2008/0249635 A1 | 10/2008 | Weitzner et al. |
| 2008/0255601 A1 | 10/2008 | Birk |
| 2008/0255678 A1 | 10/2008 | Cully et al. |
| 2008/0262529 A1 | 10/2008 | Jacques |
| 2008/0306506 A1 | 12/2008 | Leatherman |
| 2009/0012553 A1 | 1/2009 | Swain et al. |
| 2009/0082644 A1 | 3/2009 | Li |
| 2009/0093767 A1 | 4/2009 | Kelleher |
| 2009/0093837 A1* | 4/2009 | Dillon ......................... 606/191 |
| 2009/0131968 A1 | 5/2009 | Birk |
| 2009/0132031 A1 | 5/2009 | Cook |
| 2009/0149879 A1* | 6/2009 | Dillon ......................... 606/192 |
| 2009/0177215 A1 | 7/2009 | Stack |
| 2009/0198210 A1 | 8/2009 | Burnett et al. |
| 2009/0216337 A1 | 8/2009 | Egan |
| 2009/0259246 A1 | 10/2009 | Eskaros et al. |
| 2009/0275973 A1 | 11/2009 | Chen et al. |
| 2009/0287231 A1 | 11/2009 | Brooks et al. |
| 2009/0299327 A1* | 12/2009 | Tilson et al. ................ 604/500 |
| 2009/0299486 A1 | 12/2009 | Shohat et al. |
| 2009/0312597 A1 | 12/2009 | Bar et al. |
| 2010/0030017 A1 | 2/2010 | Baker et al. |
| 2010/0049224 A1* | 2/2010 | Vargas .......................... 606/153 |
| 2010/0081991 A1* | 4/2010 | Swisher .................... 604/101.05 |
| 2010/0082047 A1 | 4/2010 | Cosgrove |
| 2010/0087843 A1 | 4/2010 | Bertolote |
| 2010/0100079 A1 | 4/2010 | Berkcan |
| 2010/0100115 A1 | 4/2010 | Soetermans et al. |
| 2010/0121371 A1 | 5/2010 | Brooks et al. |
| 2010/0168782 A1 | 7/2010 | Hancock |
| 2010/0168783 A1 | 7/2010 | Murature |
| 2010/0174307 A1 | 7/2010 | Birk |
| 2010/0198249 A1* | 8/2010 | Sabliere ........................ 606/192 |
| 2010/0234937 A1 | 9/2010 | Wang |
| 2010/0249822 A1 | 9/2010 | Nihalani |
| 2010/0249825 A1 | 9/2010 | Nihalani |
| 2010/0256775 A1 | 10/2010 | Belhe et al. |
| 2010/0256776 A1 | 10/2010 | Levine et al. |
| 2010/0261390 A1 | 10/2010 | Gardner |
| 2010/0274194 A1 | 10/2010 | Sobelman |
| 2010/0286628 A1 | 11/2010 | Gross |
| 2010/0305590 A1 | 12/2010 | Holmes et al. |
| 2010/0331756 A1 | 12/2010 | Meade et al. |
| 2010/0332000 A1 | 12/2010 | Forsell |
| 2011/0009897 A1 | 1/2011 | Forsell |
| 2011/0106113 A1 | 5/2011 | Tavakkolizadeh |
| 2011/0307075 A1 | 12/2011 | Sharma |
| 2012/0022561 A1 | 1/2012 | Forsell |
| 2012/0095483 A1 | 4/2012 | Babkes |
| 2012/0221037 A1 | 8/2012 | Birk |

FOREIGN PATENT DOCUMENTS

| | | |
|---|---|---|
| DE | 8804765 U1 | 5/1989 |
| DE | 102007025312 | 11/2008 |
| EP | 1396242 A1 | 3/2004 |
| EP | 1396243 A1 | 3/2004 |
| EP | 1397998 | 3/2004 |
| EP | 1774929 | 4/2007 |
| EP | 2095798 | 9/2009 |
| FR | 2797181 A1 | 2/2001 |
| FR | 2823663 A1 | 10/2002 |
| FR | 2852821 A1 | 10/2004 |
| FR | 2855744 A1 | 12/2004 |
| FR | 2892297 | 4/2007 |
| FR | 2941617 | 8/2010 |
| GB | 2086792 A | 5/1982 |
| JP | S63279854 A | 11/1988 |
| JP | 1049572 A | 2/1989 |
| JP | 63264078 | 10/1998 |
| WO | 8800027 | 1/1988 |
| WO | WO 8800027 | 1/1988 |
| WO | 0015158 A1 | 3/2000 |
| WO | 0032092 | 6/2000 |
| WO | 0110359 A1 | 2/2001 |
| WO | 0149245 A2 | 7/2001 |
| WO | 0166166 A2 | 9/2001 |
| WO | 0235980 A2 | 5/2002 |
| WO | 03055419 A1 | 7/2003 |
| WO | 03105732 A1 | 12/2003 |
| WO | 2004019671 A2 | 3/2004 |
| WO | 2005007231 A1 | 1/2005 |
| WO | 2005094257 | 10/2005 |
| WO | WO 2005/097012 | 10/2005 |
| WO | WO 2005/110280 | 11/2005 |
| WO | 2006044640 | 4/2006 |
| WO | 2006020370 | 6/2006 |
| WO | 2006063593 A2 | 6/2006 |
| WO | 2006090018 A1 | 8/2006 |
| WO | WO 2006/111961 | 10/2006 |
| WO | WO 2006/118744 | 11/2006 |
| WO | WO 2007/027812 | 3/2007 |
| WO | WO 2007053556 | 5/2007 |
| WO | 2007076021 | 7/2007 |
| WO | WO 2007/092390 | 8/2007 |
| WO | WO 2007/110866 | 10/2007 |
| WO | 2008101048 | 8/2008 |
| WO | WO 2008/112894 | 9/2008 |
| WO | WO 2008/132745 | 11/2008 |
| WO | WO 2010/042062 | 4/2010 |

(56) References Cited

FOREIGN PATENT DOCUMENTS

| WO | WO 2010/074712 | 7/2010 |
|----|----------------|--------|
| WO | WO 2010/087757 | 8/2010 |
| WO | WO 2010/117641 | 10/2010 |

OTHER PUBLICATIONS

Baggio et al. 'Biology of Integrins: GLP-1 and GIP'; Gastroenrology; V. 132; pp. 2131-2157; 2007.

Berne et al; 'Physiology'; V. 5; pp. 55-57, 210, 428, 540, 554, 579, 584, 591; 2004.

Boulant et al.; 'Cholecystokinin in Transient Lower Oesophageal Sphincter Relation Due to Gastric Distension in Humans'; Gut; V. 40; pp. 575-581; 1997.

Bradjewin et al; 'Dose Ranging Study of the Effects of Cholecystokinin in Healthy Volunteers'; J. Psychiatr. Neurosci.; V. 16 (2); pp. 91-95; 1991.

Chaudhri; 'Can Gut Hormones Control Appetite and Prevent Obesity'?' Diabetes Care; V. 31; Supp 2; pp. S284-S289; Feb. 2008.

Cohen et al.; 'Oxyntomodulin Suppresses Appetite and Reduces Food in Humans'; J. Clin. Endocrinol. Metab.; V. 88; pp. 4696-4701; 2003.

Dakin et al.; 'Oxyntomodulin Inhibits Food Intake in the Rat'; Endocrinology; V. 142; pp. 4244-4250; 2001.

Dakin et al.; 'Peripheral Oxyntomodulin Reduces Food Intake and Body Weight gain in Rats'; Endocrinology; V. 145; No. 6; pp. 2687-2695; Jun. 2004.

Davison; 'Activation of Vagal-Gastric Mechanoreceptors by Cholecystokinin'; Proc. West. Pharmocol. Soc; V. 29; pp. 363-366; 1986.

Ekblad et al.; 'Distribution of Pancreatic Peptide and Peptide-YY'; Peptides; V. 23; pp. 251-261;2002.

Greenough et al.; 'Untangling the Effects of Hunger, Anxiety and Nausea on Energy Intake During Intravenous Cholecystokinin Octapeptide (CCK-8) Infusion' Physiology and Behavior; V. 65 (2); pp. 303-310; 1998.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Houpt; 'Gastrointestinal Factors in Hunger and Satiety'; Neurosci. and Behav. Rev.; V. 6; pp. 145-164; 1982.

Kissileff et al.; 'Peptides that Regulate Food Intake: Cholecystokinin and Stomach Distension Combine to Reduce Food Intake in Humans'; Am. J. Physiol. Regul. Integr. Comp. Physiol.; V. 285; pp. 992-998; 2003.

Naslund et al.; 'Prandial Subcutaneous Injection of Glucagon-Like Peptide'; Br. J. Nutr.; V. 91; pp. 439-446; 2004.

Renshaw et al. 'Peptide YY: A Potential Therapy for Obesity'; Current Drug Targets; V. 6; pp. 171-179; 2005.

Verdich et al. 'A Meta-Analysis of the Effect of Glucagon-Like-Peptide-1 (7-36) Amide on ad Libitum Energy Intake in Humans'; J. Clin. Endocrinal. Metab. V. 86; pp. 4382-4389; Sep. 2001.

Wynne et al.; 'Subcutaneous Oxyntomodulin Reduces Body Weight in Overweight and Obese Subiects: A Double-Blind Randomized, Controlled Trial': Diabetes; V. 54; pp. 2390-2395; 2005.

BIB Bioenterics Intragastric Balloon Program, 'Take Control of Your Weight and Your Life/The Solution for You,' Inamed Health, pp. 1-2; Jan. 19, 2004.

BIB Bioenterics Intragastric Balloon Program, 'Taking the Next Step/Take Control of Your Weight and Your Life,' Inamed Health, pp. 1-9; Apr. 29, 2004.

BIB Data Sheet Directions for Use, 'BioEnterics Intragastric Balloon System,'Inamed Health, 1-12 pp.

'Living With the BIB/BioEnterics Intragastric Balloon Program,' Inamed Health; 1-10 Patient Information Brochure; pp.; May 1, 2005.

* cited by examiner

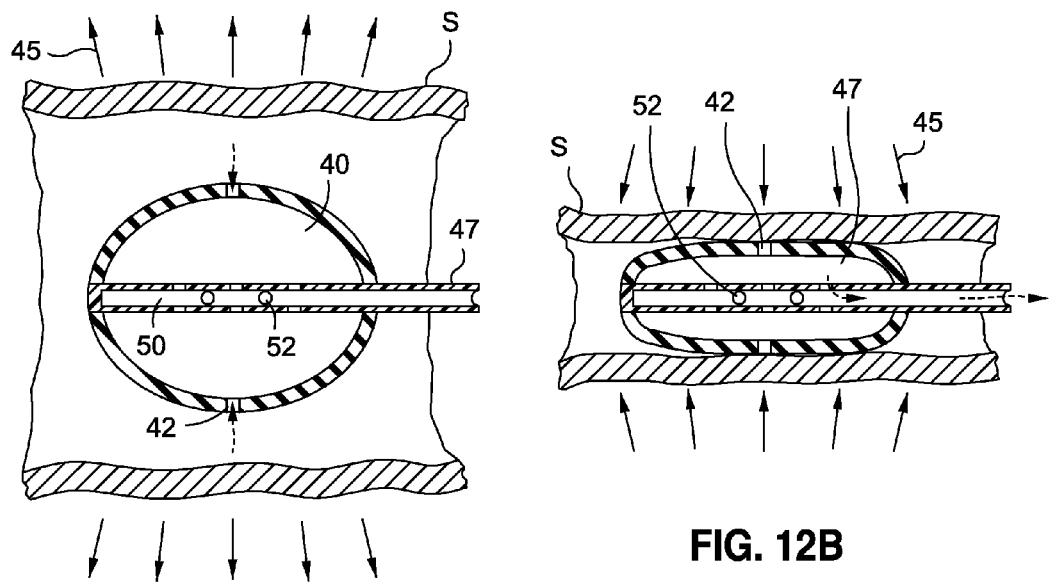
FIG. 12A
FIG. 12B
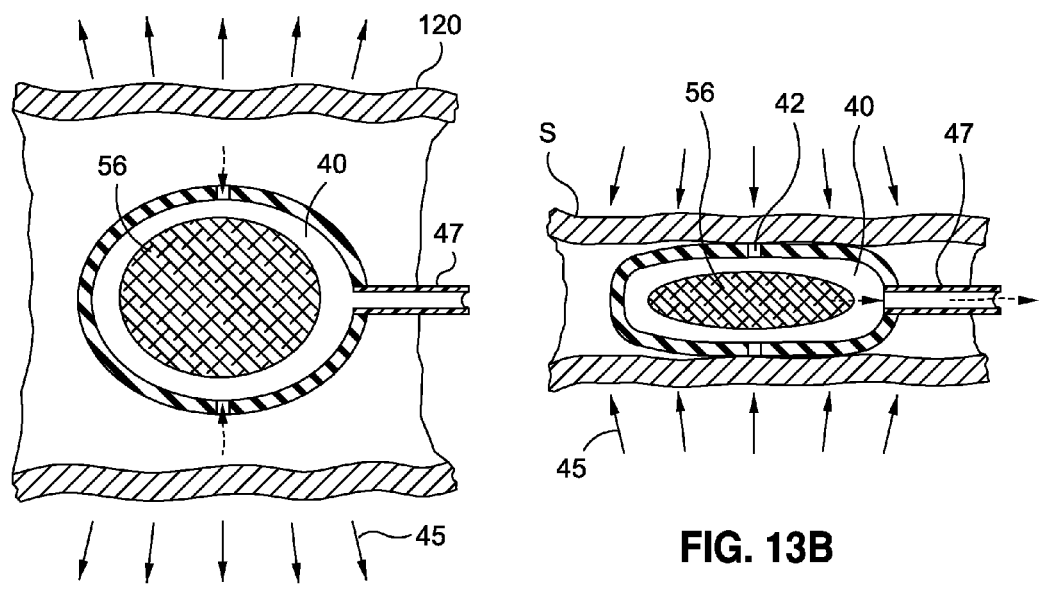
FIG. 13A
FIG. 13B

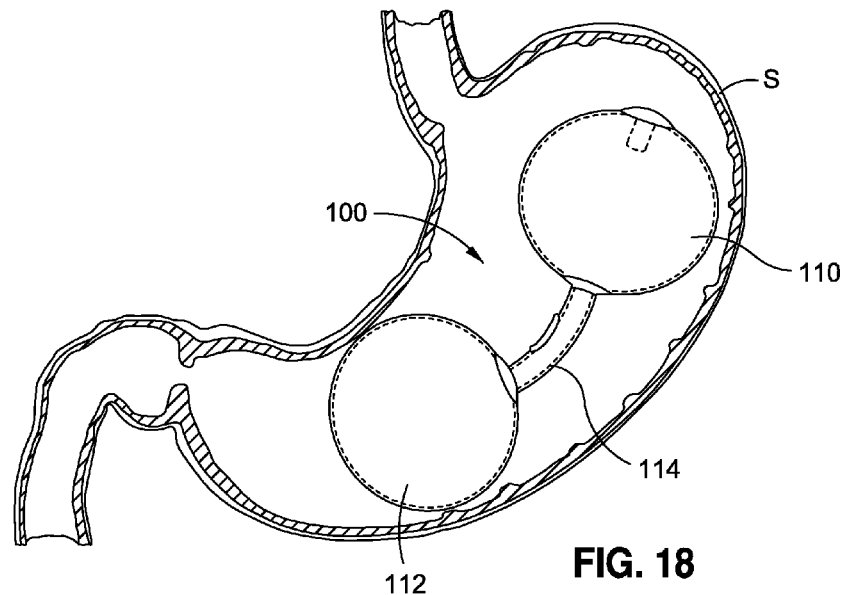
FIG. 18
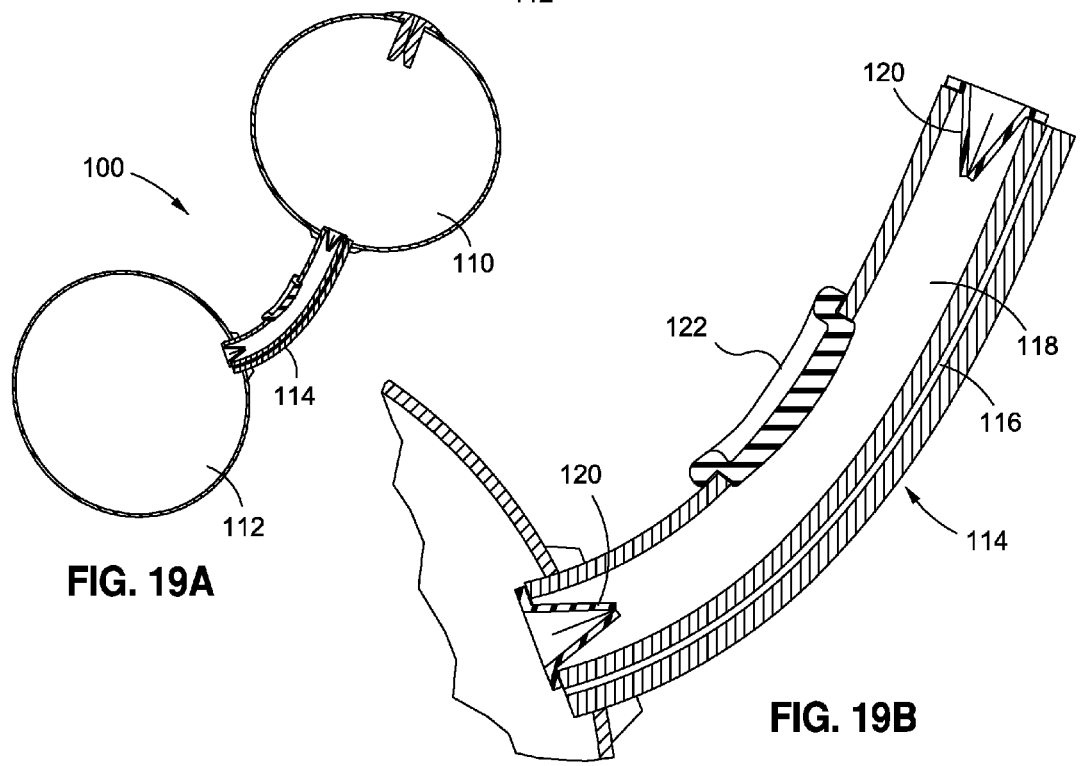
FIG. 19A
FIG. 19B

INTRAGASTRIC IMPLANTS WITH MULTIPLE FLUID CHAMBERS

RELATED APPLICATIONS

The present application claims priority under 35 U.S.C. §119 to U.S. Provisional Application No. 61/478,013, filed Apr. 21, 2011, to U.S. Provisional Application 61/394,685, filed Oct. 19, 2010, and to U.S. Provisional Application No. 61/394,592, filed Oct. 19, 2010, the disclosures of which are incorporated by reference herein.

FIELD OF THE INVENTION

The present invention generally relates to intragastric implants used for the treatment of obesity, and in particular to inflatable implants and systems for placement in the stomach cavity that provide flow between multiple chambers.

BACKGROUND OF THE INVENTION

Over the last 50 years, obesity has been increasing at an alarming rate and is now recognized by leading government health authorities, such as the Centers for Disease Control (CDC) and National Institutes of Health (NIH), as a disease. In the United States alone, obesity affects more than 60 million individuals and is considered the second leading cause of preventable death. Worldwide, approximately 1.6 billion adults are overweight, and it is estimated that obesity affects at least 400 million adults.

Obesity is caused by a wide range of factors including genetics, metabolic disorders, physical and psychological issues, lifestyle, and poor nutrition. Millions of obese and overweight individuals first turn to diet, fitness and medication to lose weight; however, these efforts alone are often not enough to keep weight at a level that is optimal for good health. Surgery is another increasingly viable alternative for those with a body mass index (BMI) of greater than 40. In fact, the number of bariatric surgeries in the United States was estimated to be about 400,000 in 2010.

Examples of surgical methods and devices used to treat obesity include the LAP-BAND® (Allergan, Inc., Irvine, Calif.) gastric band and the LAP-BAND AP® (Allergan, Inc., Irvine, Calif.) gastric band. However, surgery might not be an option for every obese individual; for certain patients, non-surgical therapies or minimal-surgery options are more effective or appropriate.

Intragastric balloons are also well known in the art as a means for treating obesity. One such inflatable intragastric balloon is described in U.S. Pat. No. 5,084,061 and is commercially available as the Orbera® System from Allergan Medical of Irvine, Calif. These devices are designed to provide therapy for moderately obese individuals who need to shed pounds in preparation for surgery, or as part of a dietary or behavioral modification program.

The Orbera® System, for example, consists of a silicone elastomer intragastric balloon that is inserted into the stomach in an empty or deflated state and thereafter filled (fully or partially) with a suitable fluid. The balloon occupies space in the stomach, thereby leaving less room for food and creating a feeling of satiety for the patient. Placement of the intragastric balloon is non-surgical, trans-oral, usually requiring no more than 20-30 minutes. The procedure is performed gastroscopically in an outpatient setting, typically using local anesthesia and sedation. Intragastric balloons typically are implanted for a finite period of time, up to six months. Removing the balloon requires deflation by puncturing with a gastroscopic instrument, and either aspirating the contents of the balloon and removing it, or allowing the fluid to pass into the patient's stomach. Clinical results with these devices show that for many obese patients, the intragastric balloons significantly help to control appetite and accomplish weight loss.

Some attempted solutions for weight loss by placing devices in the stomach result in unintended consequences. For instance, some devices tend to cause food and liquid to back up in the stomach, leading to symptoms of gastroesophageal reflux disease (GERD), a condition in which the stomach contents (food or liquid) leak backwards from the stomach into the esophagus. Also, the stomach acclimates to some gastric implant devices, leading to an expansion of stomach volume and consequent reduction in the efficacy of the device.

Despite the advances in the design of intragastric balloons, there remains a need for improved intragastric obesity treatment implants that provide more varied stimulation.

SUMMARY OF THE INVENTION

The present invention addresses the above-described problems by providing intragastric apparatuses and methods for inducing satiety and therefore treating obesity. The devices may take up volume within the stomach, thus reducing the intake capacity. Additionally, the devices may contact areas within the stomach, such as the cardia surrounding the esophageal sphincter, to stimulate satiety-inducing nerves. Also, a number of devices slow gastric emptying by blocking or otherwise impeding flow through the pyloric sphincter. A number of devices combine two or more of these satiety-inducing features. Methods of implant are disclosed including compressing the devices within a delivery tube and transorally advancing the devices through the esophagus to be deployed within the stomach. Removal of the devices occurs in the reverse.

One intragastric obesity treatment implant disclosed herein comprises a first inflatable balloon configured to be disposed in a patient's stomach, wherein the first inflatable balloon is configured to be inflated with a fluid after implantation in the patient's stomach. A second inflatable balloon fluidly couples to the first inflatable balloon such that the inflatable balloons have a longitudinal length that substantially spans the stomach and the second inflatable balloon is positioned adjacent the cardia, wherein the second inflatable balloon is configured to be inflated with a fluid after implantation in the patient's stomach. A flow restrictor interposed between the first and second inflatable balloons regulates flow therebetween. In response to peristaltic inward pressure from the stomach proximate the first inflatable balloon, a portion of the fluid moves from the first inflatable balloon through the flow restrictor into the second inflatable balloon and causes the second inflatable balloon to expand to exert pressure on the cardia and induce a feeling of satiety in the patient.

The first inflatable balloon and the second inflatable balloon may comprise a plurality of external grooves oriented along an axis connecting the two balloons and configured to allow ingested food to pass by so that the ingested food may be digested by the patient. The first and second inflatable balloons may have eight grooves each. In one embodiment, the flow restrictor comprises a narrow portion connecting the first inflatable balloon and the second inflatable balloon, and further including an elastic band wrapped around the narrow portion. Alternatively, wherein the flow restrictor comprises a narrow portion connecting the first inflatable balloon and the second inflatable balloon, and the narrow portion includes fluted wings configured to provide structural support to the narrow portion.

The implant may further include a single evacuation valve that may be accessed with an aspirator to simultaneously evacuate both the first and second inflatable balloons. In one form, the implant has a dog-bone shape, with identical first and second inflatable balloons defining enlarged outer ends joined by a smaller middle portion. Also, the first and second inflatable balloons may each include an inner end wall diametrically-oriented with respect to the longitudinal axis, the end walls being joined in abutting relationship to form a partition in the implant, and wherein the flow restrictor comprises fluid passageways across the partition. A valve may be positioned in the partition that permits flow from the first inflatable balloon to the second inflatable balloon but prevents reverse flow therebetween, the valve having a flow rate capacity greater than the fluid passageways of the flow restrictor. The first and second inflatable balloons may have a generally uniform longitudinal exterior shape.

In one embodiment, the second inflatable balloon is at least three times the volume of the first inflatable balloon. Desirably, the combined volumes of the first and second inflatable balloons is at least about 400 ml of saline. The implant may further including a tether having a first fluid passage fluidly connecting the first and second inflatable balloons and having the flow restrictor therein. The tether may include two passages, the first fluid passage being open between the first and second inflatable balloons and a second passage having one-way flow valves therein at each end adjacent each of the first and second inflatable balloons that prevent fluid from traveling from the second passage into the respective first or second inflatable balloon but permit flow from the respective first or second inflatable balloon into the second passage upon a predetermined pressure differential thereacross. The first fluid passage preferably has a size that permits a maximum flow rate of about 1-20 ml/s.

The implant may also include a third inflatable balloon positioned between the first and second inflatable balloons, the third inflatable balloon having a fixed volume and not being freely fluidly connected to the first and second inflatable balloons. The third inflatable balloon preferably comprises a larger balloon than either of the first and second inflatable balloons, wherein the first and second inflatable balloons fluidly communicate with each other via a communication tube extending through the third inflatable balloon. A relief valve may be provided on the communication tube and within the third inflatable balloon that opens from a threshold pressure from the connected first and second inflatable balloons to vent fluid into the third inflatable balloon.

Another aspect of the application is an intragastric obesity treatment implant having an outer inflatable balloon configured to be disposed in a patient's stomach, wherein the outer inflatable balloon is configured to be inflated with saline after implantation in the patient's stomach and having a length oriented along a longitudinal axis that substantially spans the stomach such that a first end of the implant is positioned adjacent the antrum and a second end of the implant is positioned adjacent the cardia. A core balloon located within the outer inflatable balloon contains air without leaking so as to occupy volume within the outer inflatable balloon. The core balloon includes an upper portion residing within the second end of the outer balloon, and a lower portion residing within the first end of the outer balloon having a smaller internal volume than the upper portion such that the greater buoyancy of the upper portion tends to orient the second end of the outer balloon at the top of the stomach cavity adjacent the cardia.

The upper portion may be formed as a monolithic bladder and the lower portion of the core balloon comprises a series of elongated longitudinally-oriented bladders fluidly connected to the single monolithic bladder. The outer inflatable balloon preferably includes first and second inflatable balloons respectively defining the first and second ends of the implant and separated from each other by a one-way valve and a series of fluid passageways. The one-way valve permits fluid flow of a predetermined maximum rate from the first inflatable balloon to the second inflatable balloon and the fluid passageways permitting fluid flow in the opposite direction from the second inflatable balloon to the first inflatable balloon at a rate less than the predetermined maximum rate. Consequently, in response to peristaltic inward pressure from the stomach proximate the first inflatable balloon, a portion of the fluid moves from the first inflatable balloon through the one-way valve into the second inflatable balloon and causes the second inflatable balloon to expand to exert pressure on the cardia and induce a feeling of satiety in the patient.

In one embodiment, each of the first and second inflatable balloons includes an inner end wall diametrically-oriented with respect to the longitudinal axis, the end walls being joined in abutting relationship to form a partition in the implant, and wherein the one-way valve and fluid passageways cross the partition. The core balloon may span the partition. The implant may further have an outer fill valve in the outer inflatable balloon at the first end of the implant with an outlet aperture projecting within the outer inflatable balloon and toward an inner fill valve in the core balloon such that a single fill tube may be used to inflate both the inner core balloon with air and the outer inflatable balloon with saline.

An alternative embodiment of an intragastric obesity treatment implant comprises a pumping chamber configured to pump a fluid within a patient's stomach, wherein the fluid enters the pumping chamber via a hole disposed in the pumping chamber. A first reservoir couples to the pumping chamber via first tubing, and a first fill valve disposed in the first reservoir couples to the first tubing to regulate the flow of the fluid from the pumping chamber to the first reservoir. Consequently, a peristaltic motion of the patient's stomach compresses the pumping chamber causing the fluid to exit the pumping chamber through the first tubing and the first fill valve into the first reservoir. The implant also has a first release valve disposed in the first reservoir, wherein the first release valve is configured to release a portion of the fluid from the first reservoir when a first predetermined condition is reached in the first reservoir.

A still further intragastric obesity treatment implant disclosed herein has a flexible pumping chamber with a fill valve and configured to be inserted transorally into a patient's stomach in a deflated state and inflated with a fluid through the fill valve. First and second flexible reservoirs each separately fluidly couple to the pumping chamber via an open fluid transfer lumen. A fill valve fluidly disposed in a fluid lumen between each of the first and second reservoirs and the pumping chamber permits the flow of the fluid from the pumping chamber to the respective reservoir but prevents flow in the opposite direction.

In either of the preceding two implants with pumping chambers, a second reservoir may be provided comprising a second fill valve, wherein the second reservoir is coupled to the pumping chamber via second tubing. The pumping chamber, the first reservoir, and the second reservoir may be coupled in series or in parallel. The first fill valve and the second fill valve may individually comprise at least one of a one-way valve, a duckbill valve, or a ball check valve. Preferably, at least one of the first reservoir or the second reservoir comprises a compliant reservoir that expands in response to the fluid entering the compliant reservoir, wherein the expanding compliant reservoir generates an increased pressure in the compliant reservoir. The implant may have a second release valve disposed in the second reservoir to release a second portion of the fluid from the second reservoir when a second predetermined condition is reached in the second reservoir. The first release valve and the second release valve may individually comprise at least one of a flow restrictor, a burp valve, or a burst valve. The first predetermined condition and the second predetermined condition individually comprise at least one of a predetermined pressure, a predetermined shape, or a predetermined size.

In some cases, a wall of the patient's stomach covers the hole during the peristaltic motion to cause the fluid to exit the pumping chamber via the first tubing. Or, a wall of the patient's stomach covers the hole during the peristaltic motion to prevent the fluid from exiting the hole. The pumping chamber desirably comprises a plurality of holes. The pumping chamber is preferably configured to return to an expanded state after the peristaltic motion ceases, and wherein the pumping chamber draws the fluid into the pumping chamber through the hole when the pumping chamber returns to the expanded state.

In one embodiment, the pumping chamber includes an open celled foam structure to cause the pumping chamber to return to the expanded state. The pumping chamber may also comprise thick walls that cause the pumping chamber to return to the expanded state. The pumping chamber may further comprise a chamber tube disposed through the pumping chamber to cause the pumping chamber to return to the expanded state. In one form, the chamber tube is coupled to the first tubing and comprises a chamber tube hole to allow the fluid to pass from the pumping chamber into the chamber tube and through the first tubing into the first reservoir.

The fluid may be saline, and the volume of the pumping chamber is between about 400-600 ml. Each of the fluid transfer lumens preferably has a size that permits a maximum flow rate of about 1-20 ml/s. The implant may further include a connector between each of the first and second reservoirs and the pumping chamber, including a threaded coupling through which the fluid transfer lumen and the fluid lumen pass. The fluid transfer lumen may be substantially smaller in size than the fluid lumen such that fluid flows faster from the pumping chamber to the reservoirs than in the reverse for a given pressure differential.

In another embodiment, an intragastric obesity treatment implant comprises a first inflatable balloon configured to be disposed in a patient's stomach, wherein the first inflatable balloon is configured to be inflated with a fluid after implantation in the patient's stomach. A second inflatable balloon couples to the first inflatable balloon such that the inflatable balloons have a longitudinal length that substantially spans the stomach and the second inflatable balloon is positioned adjacent the cardia, wherein the second inflatable balloon is configured to be inflated with a fluid after implantation in the patient's stomach. A flow restrictor interposed between the first and second inflatable balloons is adapted to regulate flow therebetween. In response to peristaltic movement of the stomach proximate the first inflatable balloon, a portion of the fluid moves from the first inflatable balloon through the flow restrictor into the second inflatable balloon and causes the second inflatable balloon to expand to exert pressure on the cardia and induce a feeling of satiety in the patient.

Further, in an embodiment, an intragastric obesity treatment implant comprises a pumping chamber configured to pump a fluid within a patient's stomach. The fluid enters the pumping chamber via a hole disposed in the pumping chamber. A reservoir is coupled to the pumping chamber via tubing, and a fill valve is disposed in the reservoir and coupled to the tubing to regulate the flow of the fluid from the pumping chamber to the reservoir. The peristaltic motion of the patient's stomach compresses the pumping chamber causing the fluid to exit the pumping chamber through the tubing and the fill valve into the reservoir. A release valve is disposed in the reservoir, and the release valve is configured to release a portion of the fluid from the reservoir into the patient's stomach when a predetermined condition is reached in the reservoir.

A further understanding of the nature and advantages of the invention will become apparent by reference to the remaining portions of the specification and drawings.

BRIEF DESCRIPTION OF THE DRAWINGS

FIGS. 12A-12B illustrate sectional views of a pumping chamber with a chamber tube in accordance with an embodiment of the present application.

FIGS. 13A-13B illustrate sectional views of a pumping chamber with open-celled foam in accordance with an embodiment of the present application.

FIG. 18 illustrates a side view of an intragastric obesity treatment implant with two inflated and fluidly-connected balloons in a patient's stomach in accordance with an embodiment of the present application.

FIG. 19A illustrates a sectional side view of an intragastric obesity treatment implant as in FIG. 18 showing a flow restrictor within a connecting tether.

FIG. 19B is a detail of the connecting channel from FIG. 19A showing the flow restrictor and a deflation assembly.

FIG. 26A show an alternative dual-balloon intragastric obesity treatment implant similar to that in FIGS. 25A-25B with a more uniform longitudinal shape and positioned within the stomach, while

DETAILED DESCRIPTION OF THE PREFERRED EMBODIMENTS

In accordance with various embodiments of the present application, intragastric obesity treatment implants generally comprise an implant that occupies space in a patient's stomach. The space occupied by the intragastric obesity treatment implant reduces the available volume in the stomach that may be occupied by ingested food. Accordingly, a patient with the intragastric obesity treatment implant in the stomach may experience a feeling of satiety while consuming less food than before the device was implanted. This reduced food intake may allow the patient to lose weight.

Furthermore, some embodiments disclosed herein may exert pressure on the upper portion of the stomach, or the cardia. This pressure may induce early feelings of satiety by triggering the patient's brain to release satiety-inducing hormones. These hormones may cause the patient to stop eating sooner, also resulting in weight loss.

By way of example, the present disclosure will reference and discuss certain intragastric obesity treatment implants. Nevertheless, persons skilled in the art will readily appreciate that concepts disclosed herein may be advantageously applied to arrive at other intragastric obesity treatment implants without departing from the scope of the present invention.

Various embodiments allow for the intragastric obesity treatment implants to be implanted in the patient's stomach transorally—through the patient's mouth and down the patient's esophagus. As such, the intragastric obesity treatment implants may be referred to as transoral implants and/or transoral intragastric obesity treatment implants. Transoral implantation advantageously allows implantation of the intragastric obesity treatment implant without associated patient risks of invasive surgery and without substantial patient discomfort. Recovery time after implantation of the transoral intragastric obesity treatment implant may be minimal as no extensive tissue healing is generally required. The life span of these implants may be material-dependent upon long-term survivability within an acidic stomach, but various embodiments are advantageously configured to last one year or longer.

Figure 1:
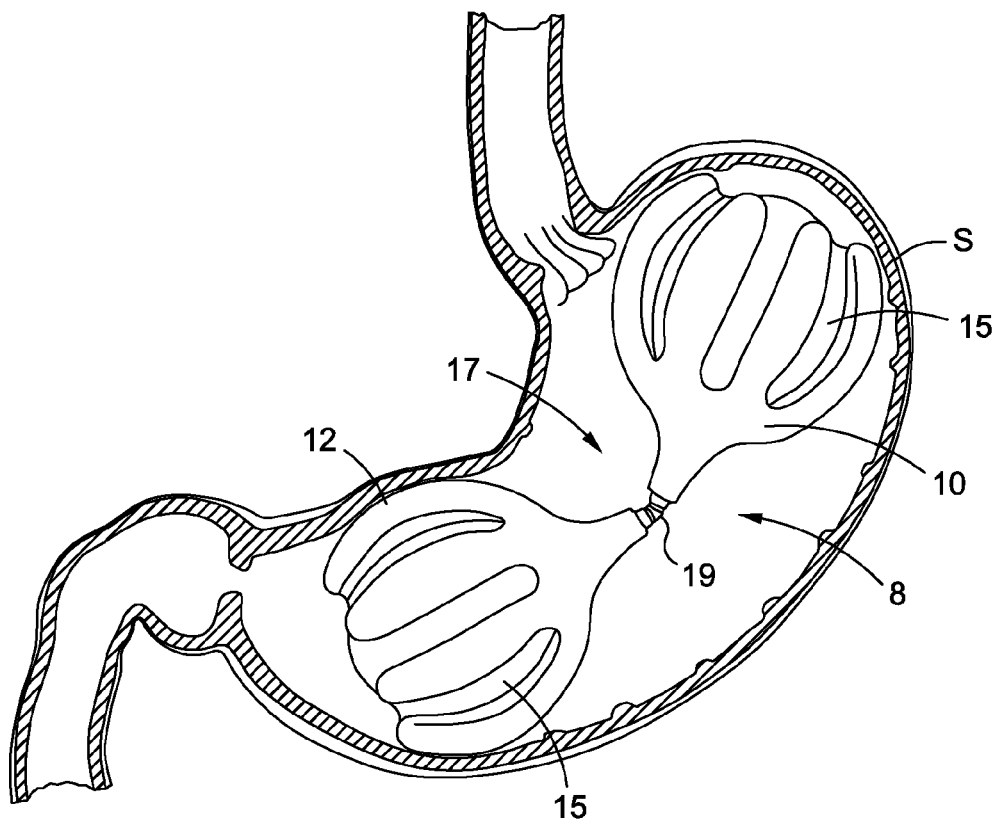
FIG. 1 illustrates a side view of an intragastric obesity treatment implant with two grooved balloons in a patient's stomach in accordance with an embodiment of the present application.
Figure 2:
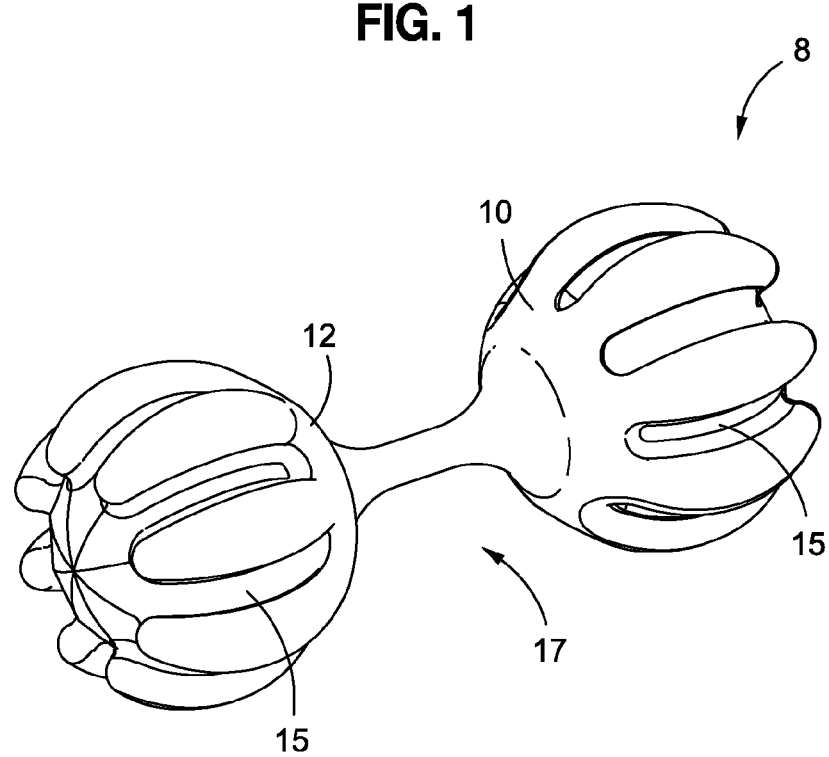
FIG. 2 illustrates a perspective view of an intragastric obesity treatment implant with two grooved balloons similar to FIG. 1.
Figure 3:
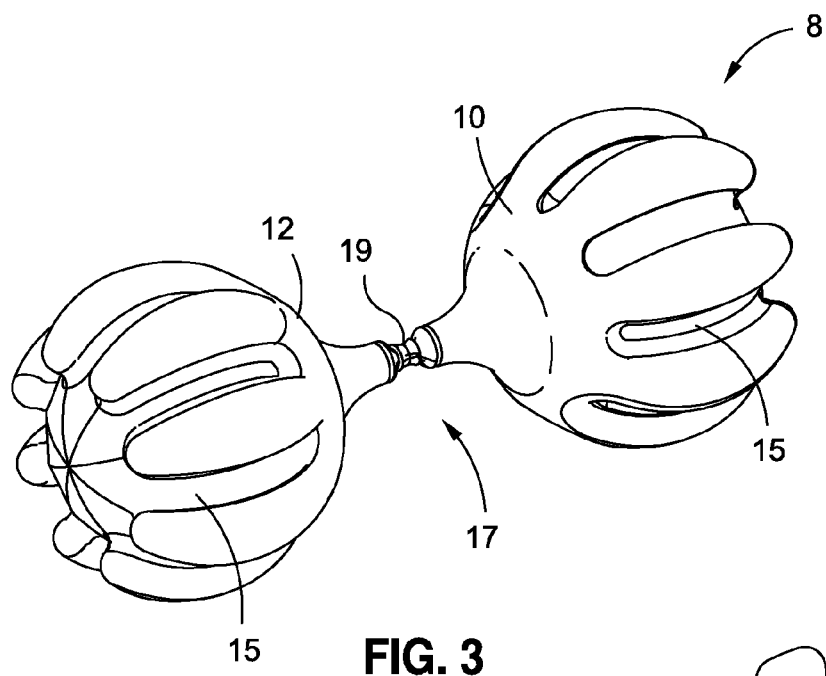
FIG. 3 illustrates a perspective view of an intragastric obesity treatment implant with two grooved balloons and a flow restrictor similar to FIG. 1.

FIG. 1 illustrates a first space-occupying implant 8, but also illustrates the anatomy of the human stomach, which will be described first. The major function of the stomach is to temporarily store food and release it slowly into the duodenum. The esophagus extending downward from the mouth connects to the stomach via esophageal sphincter, which regulates flow food into the stomach cavity. The cardia surrounds the superior opening of the stomach. The rounded portion superior to the body and adjacent the cardia is the fundus. Inferior to the fundus is the large central portion of the stomach, called the body, that is lined with muscles that contract and relax repetitively to churn the food therein. The stomach processes the food to a semi-solid "chyme," which enables better contact with the mucous membrane of the intestines, thereby facilitating absorption of nutrients. In addition, the stomach is an important site of enzyme production.

Lower down in the stomach the antrum connects the body to the pylorus, which leads into the duodenum. Below the stomach, the duodenum leads into the upper part of the small intestine (not shown); the jejunum makes up about one-third of the small intestine. The region of the stomach that connects to the duodenum is the pylorus. The pylorus communicates with the duodenum of the small intestine via the pyloric sphincter (valve). This valve regulates the passage of chyme from stomach to duodenum and it prevents backflow of chyme from duodenum to stomach.

Connected Lobes

In accordance with further embodiments of the present invention, and with reference to FIGS. 1-5, an intragastric obesity treatment implant 8, such as an active balloon adipose trimming element, comprises a gastrointestinal implant with two lobes and/or balloons 10, 12, that may be filled with saline, air, or other fluids. In an embodiment, the balloons 10, 12 have a nominal capacity (e.g., in a post-filled, pre-expanded state) of at least approximately 400 g, or about 400 ml, of saline.

The intragastric obesity treatment implant 8 may be configured to be implanted in the patient's stomach S, transorally, without invasive surgery, and without associated patient risks of invasive surgery. Recovery time may be minimal because of reduced tissue healing post implantation. In an embodiment, the intragastric obesity treatment implant 8 may have a product life span in the stomach S of up to one year or longer. As will be discussed, the intragastric obesity treatment implant 8 facilitates weight loss and obesity treatment through adipose trimming and/or fat reduction due to the patient consuming less food.

The intragastric obesity treatment implant 8 comprises an active system where the balloons 10, 12 are joined to each other and are configured to occupy space inside the stomach S, thereby decreasing the amount of food that is ingestible by the patient, which may result in weight loss. The intragastric obesity treatment implant 8 is configured to span the upper and lower stomach regions, ranging from the antrum to the cardia.

In addition to occupying space in the stomach S, the intragastric obesity treatment implant 8 may be configured to actively facilitate obesity treatment through early inducement of feelings of satiety and resulting reduced food consumption. For example, in an embodiment, a fluid is disposed in the balloons 10, 12, and the fluid may move between the balloons 10, 12 via a center portion 17 that couples the balloon 10 to the balloon 12. The center portion 17 comprises a passageway that allows the fluid to pass between the balloons 10, 12.

After ingestion of food by the patient, peristaltic digestive "churning" of the stomach S begins. These peristaltic motions cause various portions of the stomach S to repeatedly contract and relax to move food through the stomach S. Based on the geometry of the stomach S and the intragastric obesity treatment implant 8, the peristaltic motions near the lower balloon 12 (disposed near the antrum) may cause the stomach S to squeeze the balloon 12. As the balloon 12 is squeezed, fluid passes from the balloon 12, through the center portion 17, and into the upper balloon 10 (disposed near the cardia). The upper balloon 10 may comprise a compliant material, such that the increased amount of fluid in the balloon 10 causes the balloon 10 to expand and exert increased pressure on the cardia. This increased pressure on the cardia may induce early feelings of satiety by triggering the brain to release satiety-inducing hormones, so eating will likely cease and weight loss may ensue.

In accordance with various embodiments, after digestion, the peristaltic motions in the stomach cease, resulting in reduced pressure exerted on the balloon 12. This reduced pressure exerted on the balloon 12, in conjunction with the increased pressure in the balloon 10 from the increased amount of fluid in the balloon 10 (and due to forces induced in the expanded compliant material in the balloon 10 from expansion), causes the fluid in the balloon 10 to return to the balloon 12 via the center portion 17 until the pressure is substantially equalized between the two balloons 10, 12.

The return flow from the balloon 10 to the balloon 12 may be slowed down to maintain an expanded size of the balloon 10 for a longer period of time. For example, the passageway in the center portion 17 may be advantageously configured to have a sufficient size to allow for a desired flow rate. In an embodiment, the passageway may be a through hole having a diameter of approximately one millimeter. In another embodiment, a center band 19 (e.g., an elastic band) may be disposed around the center portion 17 as a flow restrictor to appropriately reduce the size of the passageway and constrict for a desired flow rate. Other flow restrictor devices such as valves, pressure reducers and the like and combinations thereof may be utilized to allow for a desired flow rate between the balloons 10, 12.

Figure 4:
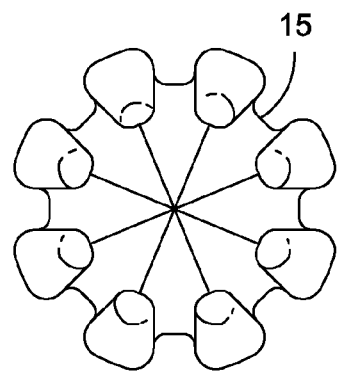
FIG. 4 illustrates an end view of the grooved intragastric obesity treatment implant balloon of FIG. 3.
Figure 5:
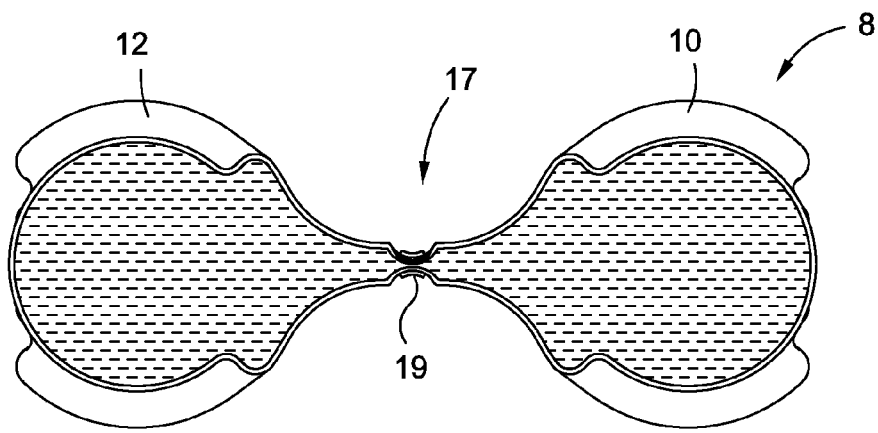
FIG. 5 illustrates a sectional side view of the intragastric obesity treatment implant with a flow restrictor of FIG. 3.

In various embodiments, the intragastric obesity treatment implant 8 may comprise a plurality of flutes, ridges, and/or grooves 15 that are configured to prevent obstruction of food as it moves through the pylorus and into the duodenum of the patient. The grooves 15 direct the food to pass by the implant 8 along the stomach S walls. For example, in an embodiment as illustrated in FIG. 4, each balloon 10, 12 comprises eight grooves 15 to direct the food flow. However, it should be understood that any number of grooves 15 that facilitate appropriate passage of food are contemplated within the scope of the present invention. The ends of the grooves 15 near the center portion 17 may be flush with the surrounding surface of the balloons 10, 12 to prevent undesired expansion from increased pressure due to movement of the fluid between the balloons 10, 12.

Figure 6A:
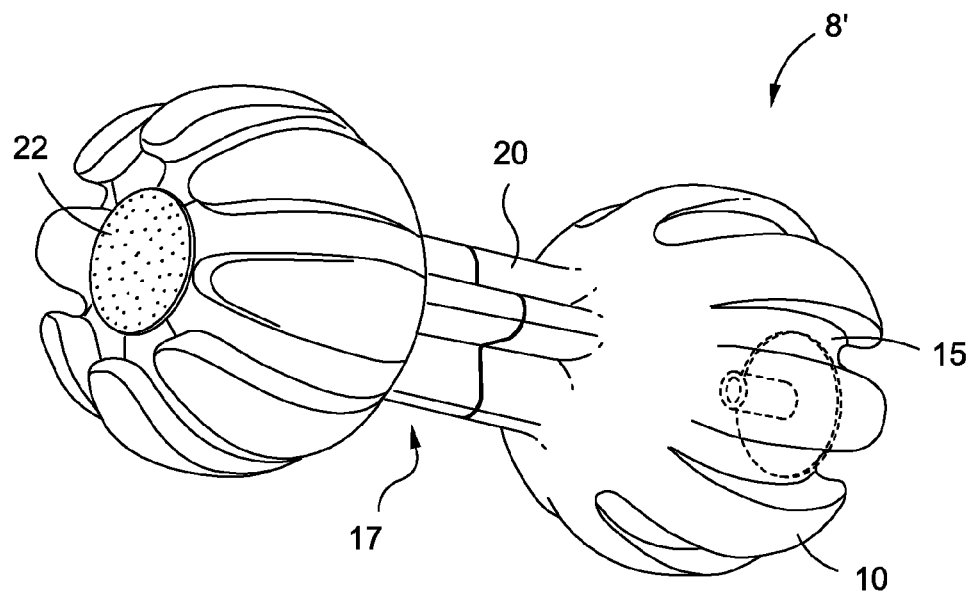
FIG. 6A illustrates a perspective view of an intragastric obesity treatment implant with center flanges and an end plug in accordance with an embodiment of the present application.
Figure 6B:
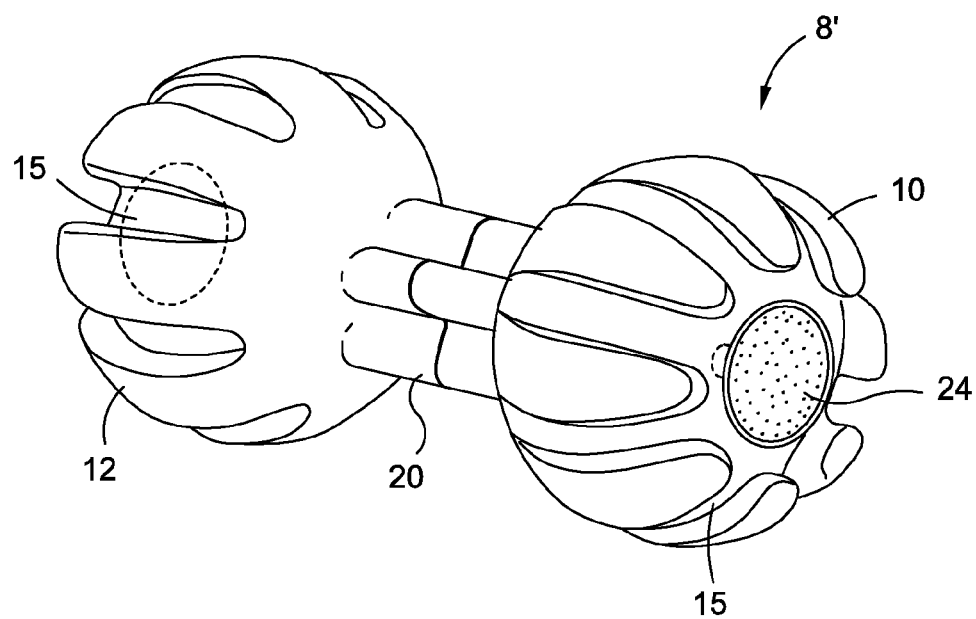
FIG. 6B illustrates a perspective view of an intragastric obesity treatment implant with center flanges and a fill valve as in FIG. 6A.
Figure 7A:
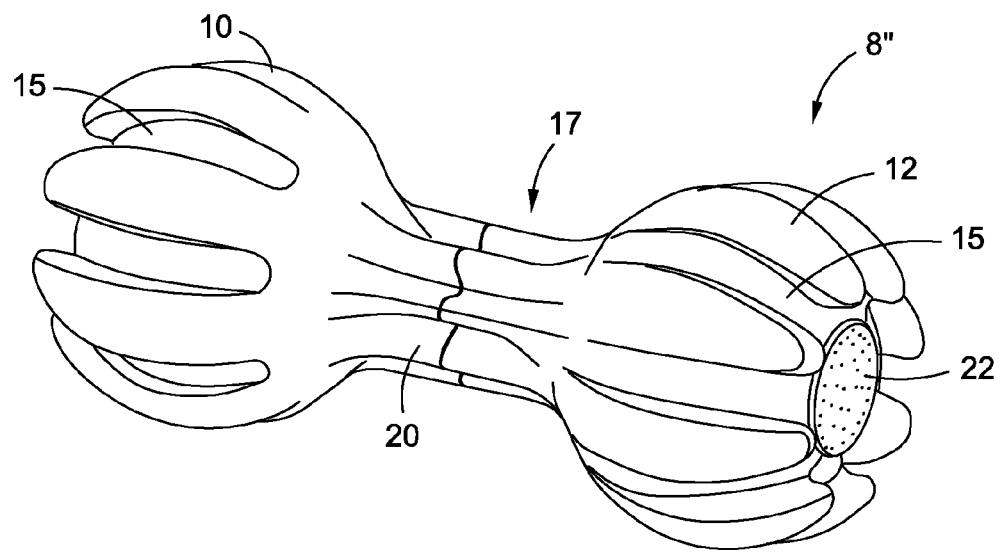
FIG. 7A illustrates a perspective view of an intragastric obesity treatment implant with eight center wings and an end plug in accordance with an embodiment of the present application.
Figure 7B:
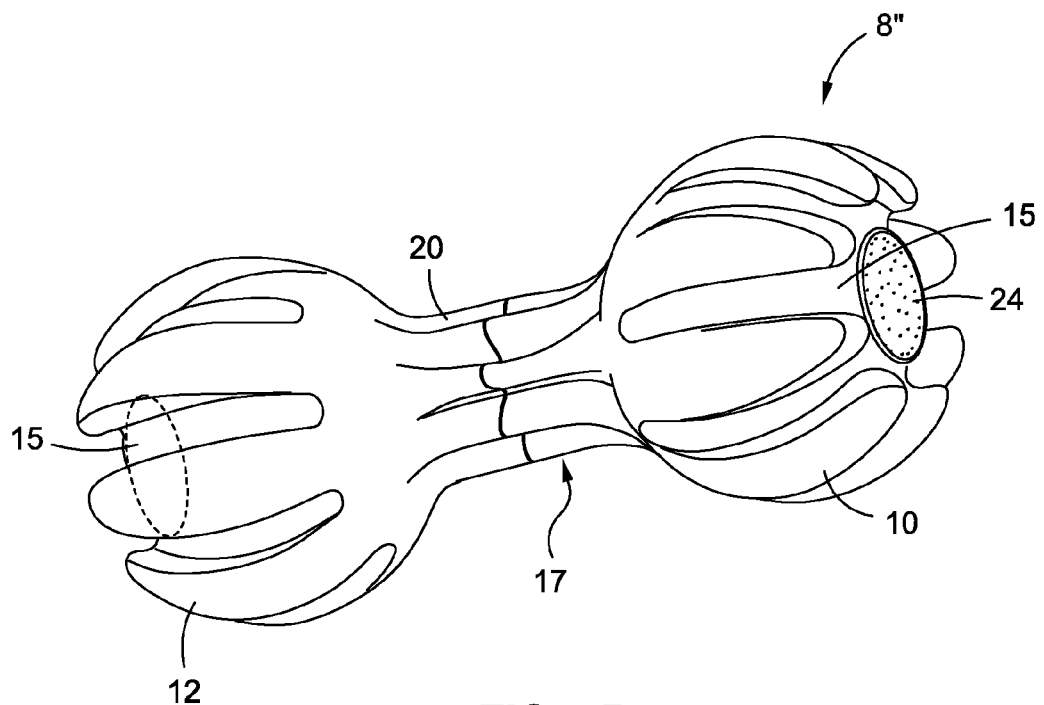
FIG. 7B illustrates a perspective view of an intragastric obesity treatment implant with eight center wings and a fill valve as in FIG. 7A.

With reference also to FIGS. 6-7, and in accordance with further embodiments, the intragastric obesity treatment implant 8 may be formed in a "dog bone" shape with enlarged ends and strengthening structure, such as a flange or wing 20 disposed along the narrower center portion 17. Although the embodiments in FIGS. 6-7 are different than those shown in FIGS. 1-5, certain common features will be given the same element numbers for clarity. The wing or wings 20 may prevent kinking of the center portion 17 in order to maintain the passageway in the center portion 17 open. For example, with reference specifically to FIGS. 6A-6B, four wings 20 may be configured in an "X" shape along the center portion 17 in accordance with an embodiment. In another embodiment, and with reference specifically to FIGS. 7A-7B, eight wings 20 may be disposed along the center portion 17 to provide structure to the center portion 17 and/or to prevent kinking. It should be understood that various other configurations of the wings 20 and/or other structures may be utilized to provide support to the center portion 17 and/or to prevent kinking, without departing from the scope of the present invention.

With continued reference to FIGS. 6-7, and in accordance with various embodiments, the balloon 10 may comprise a fill valve 24 to allow the intragastric obesity treatment implant 8 to be filled with saline after implantation of the implant in the stomach S. The balloon 12 may similarly have an end plug 22 to prevent saline from exiting the balloon 12. Thus, the intragastric obesity treatment implant 8 may be disposed in the stomach S via the esophagus in a substantially non-inflated state. In this manner, a lubricated, thin-walled tube, such as a tube made with Teflon or a similar material may be inserted through the patient's mouth, down the esophagus, and partially into the stomach S. The implant 8 in a compressed state may be preloaded into the tube prior to insertion, and may then be deployed into the stomach S after the tube is inserted.

A filling tube may be removably coupled to the intragastric obesity treatment implant 8 prior to insertion through the lubricated tube to facilitate filling the implant 8 after implantation in the stomach S. For example, the fill valve 24 may comprise a slit valve that couples the balloon 10 to the filling tube. The fill valve 24 may be a one way valve such that saline or another fluid may enter the balloon 10 via the filling tube, but the filling tube may then be removed after inflation of the intragastric obesity treatment implant 8 without a substantial amount of fluid being lost from the implant 8. After inflation, the thin-walled tube and the filling tube may be removed from the patient, leaving the inflated implant 8 in the stomach S.

To remove the intragastric obesity treatment implant 8 from the stomach, an aspirator may be fed down the patient's esophagus to puncture the implant 8, releasing the saline or other fluid into the stomach S. The deflated implant 8 may then be removed from the stomach S via the esophagus using a grasper or other tool. In various embodiments, the intragastric obesity treatment implant 8 may be configured to be removed in other ways, for example, by passing out of the patient through digestion.

Tri-Balloon Fluid Transfer Implants

Figure 8A:
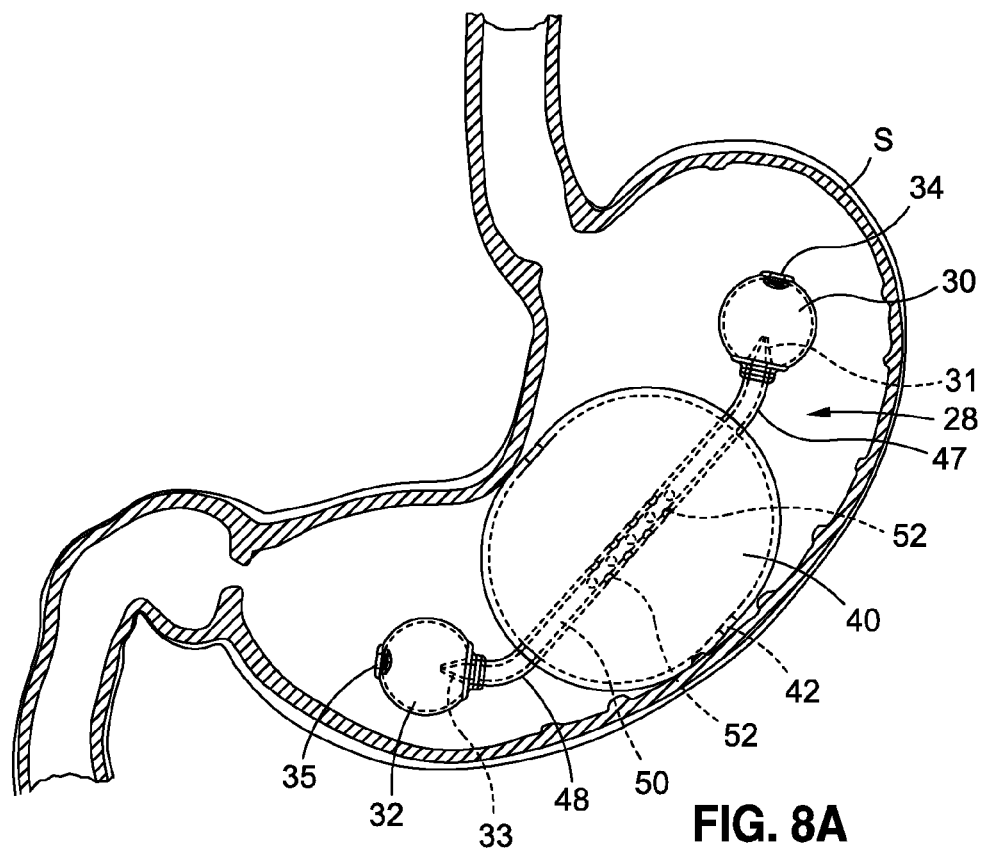
FIG. 8A illustrates a side view of an intragastric obesity treatment implant with a pumping chamber and two reservoirs in a patient's stomach in accordance with an embodiment of the present application.
Figure 8B:
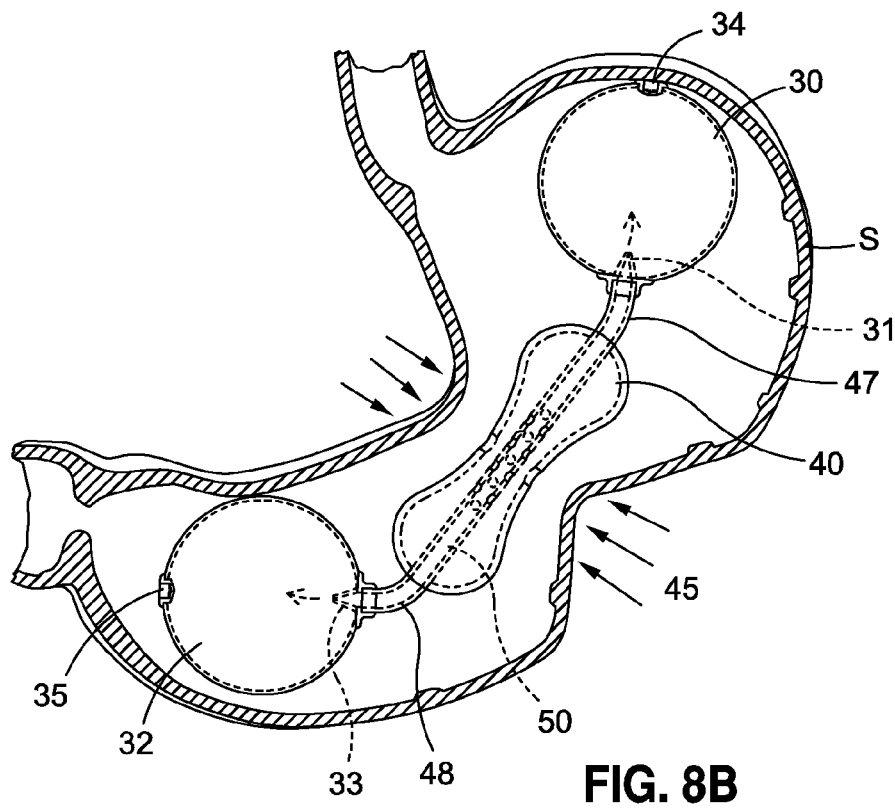
FIG. 8B illustrates a side view of an intragastric obesity treatment implant with a pumping chamber as in FIG. 8A being compressed by a patient's stomach.
Figures 9, 10A, 10B:
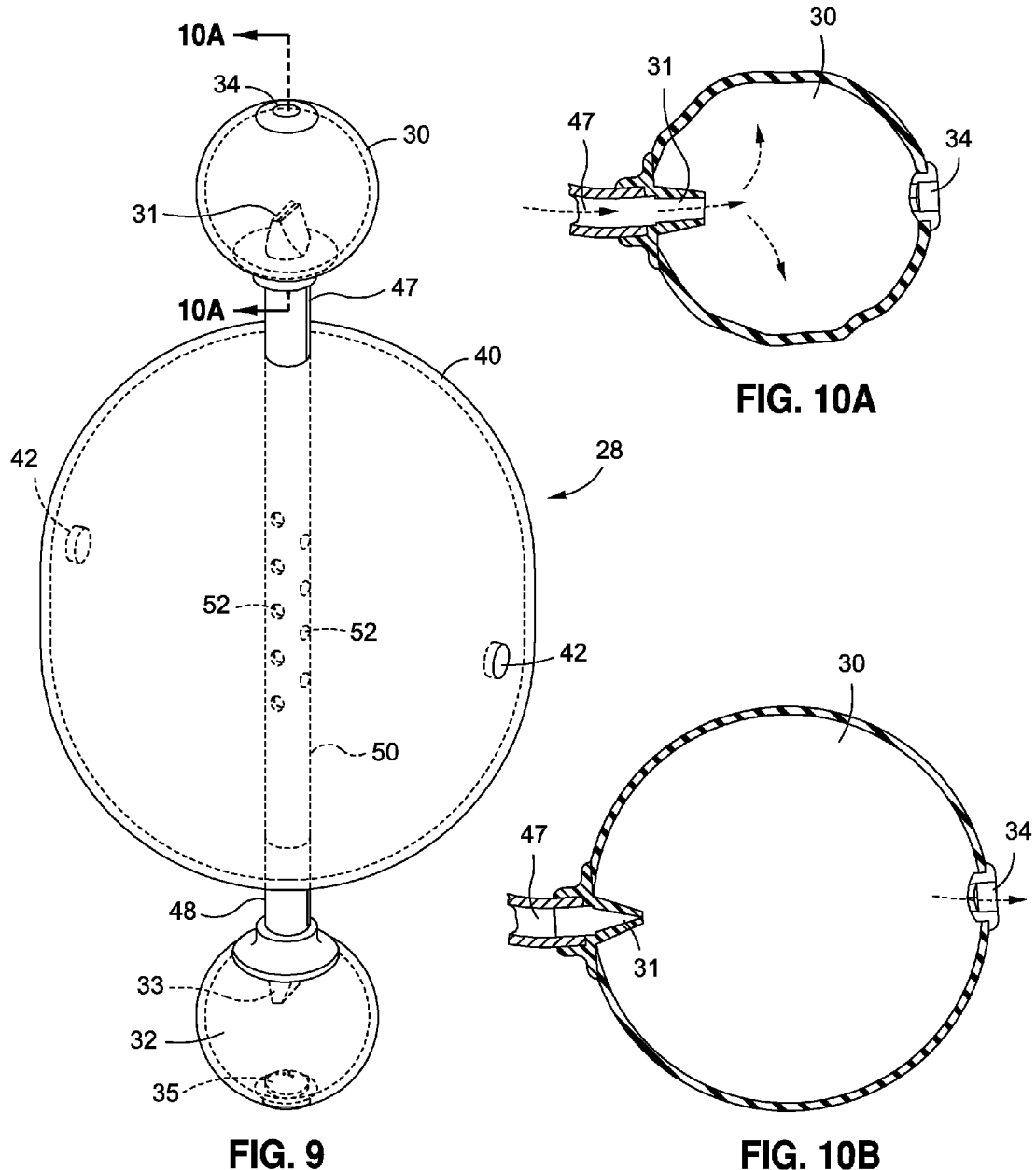
FIG. 9 illustrates a perspective view of tri-balloon intragastric obesity treatment implant with a pumping chamber, two reservoirs, one-way valves, and flow restrictors in accordance with an embodiment of the present application.
FIG. 10A illustrates a sectional view of a reservoir with an open one-way valve for use in an implant such as FIG. 9.
FIG. 10B illustrates a sectional view of a reservoir with a closed one-way valve as in FIG. 10A.

Turning now to FIGS. 8-10, an intragastric obesity treatment implant 28 will be discussed according to various embodiments of the present invention. The implant 28 is contained substantially within the patient's stomach S, and may be referred to as a stomach fluid transfer implant because it is configured to transfer stomach fluids between chambers or reservoirs to facilitate obesity control. For example, a pumping chamber 40 may move stomach fluids or juices between one or more stimulation reservoirs, such a reservoir 30.

Although various embodiments include one, two or more reservoirs (see, e.g., various configurations in FIGS. 30A-30D), it should be understood that any number of reservoirs may be utilized to facilitate obesity control without departing from the scope of the present invention. The intragastric obesity treatment implant 28 may be implanted in a similar manner as discussed above for other intragastric obesity treatment implants, for example, transorally, through the esophagus, and into the stomach, during a minimally invasive gastroendoscopic surgical procedure.

The intragastric obesity treatment implant 28 may induce weight loss through a variety of methods. In an embodiment, the volume of the implant 28 in the stomach S may reduce the total quantity of food ingested during a meal and reduce the sensation of pre-prandial hunger while implanted. In another embodiment, the implant 28 may be configured to change shape or size when acted upon by the stomach S, for example, when acted upon by peristaltic motions 45 of the stomach S during digestion. Such changes may induce a changing sensation on the stomach S, and the changing sensation may be mechanotransduced by the stomach S to trigger the efferent nerves in the stomach S so as to encourage feelings of satiety.

In accordance with various embodiments, and with continued reference to FIGS. 8-10, the pumping chamber 40 is coupled to an upper reservoir 30 via an upper tube 47 and to a lower reservoir 32 via a lower tube 48. The tubing 47, 48 may comprise rigid or flexible tubing, and may connect the various reservoirs 30, 32 in series or parallel. For example, as illustrated in FIGS. 30A-30D, reservoirs 330 may be connected by tubing 350 in series or in parallel with an alternate pumping chamber 320.

With reference back to FIGS. 8-10, and in accordance with various embodiments, the pumping chamber 40 moves fluid (e.g., gas, liquid, and combinations thereof) into the reservoirs 30, 32. For example, the pumping chamber 40 moves any fluid (liquid or gas) that is inside of the stomach. A hole 42 or plurality of holes 42 is disposed in the walls of the pumping chamber 40 to allow the stomach fluids to enter the pumping chamber 40. The reservoirs 30, 32 are compliant chambers that may expand to accommodate the volume of fluid being pumped from the pumping chamber 40. In various embodiments, the reservoirs 30, 32 may be spherical or cylindrical (see, e.g., the reservoirs 330 illustrated in FIGS. 30A-30D in accordance with various embodiments), or any other shape configured to allow fluid to enter and to exert appropriate pressure on the stomach S.

In an embodiment, when the stomach S is at rest between meals, and when the peristaltic motions 45 are not occurring, the holes 42 in the pumping chamber 40 are open, which allows the stomach juices to enter the pumping chamber 40. Then, as the peristaltic motions 45 begin during digestion, the holes 42 are configured to be covered by the stomach S walls to prevent the stomach juices from exiting the pumping chamber 40. In this manner, the peristaltic motions 45 compress the pumping chamber 40 and move the stomach juices from the pumping chamber 40, through the tubes 47, 48 and into the reservoirs 30, 32 to facilitate inducing a sensation of satiety in the patient. It should be noted that FIG. 8B is illustrative of the peristaltic motions 45 and the resulting compression of the pumping chamber 40. While FIG. 8B may appear to not show coverage of the holes 42 during the peristaltic motions 45, it should be understood that the holes 42 are covered by the stomach S walls during the compression process. After the peristaltic motions 45 stop, the stomach S relaxes, the holes 42 are uncovered, and more stomach juices enter the pumping chamber 40.

Figure 15A:
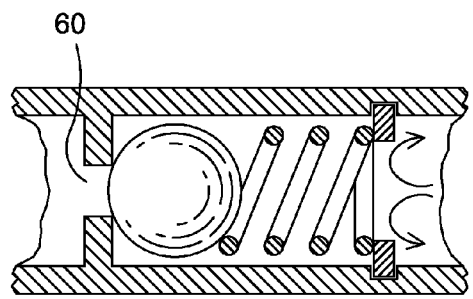
FIGS. 15A-15B illustrate sectional views of a one-way ball check valve for use in implants of the present application.
Figure 15B:
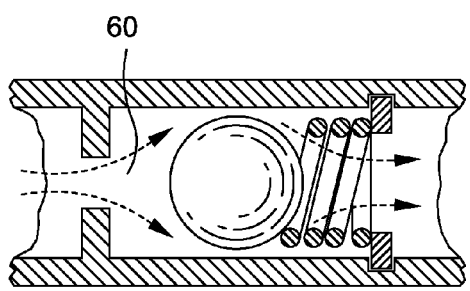

To regulate the flow of the fluids, and in accordance with various embodiments, valves 31, 33 may be coupled to the reservoirs 30, 32 and/or to the tubing 47, 48. These valves 31, 33, in accordance with an embodiment, are one-way valves to allow the fluid to flow into the reservoirs 30, 32 from the pumping chamber 40, but not from the reservoirs 30, 32 into the pumping chamber 40. In various embodiments, as illustrated in FIGS. 8-10 and 14A-14B, the valves 31, 33 may comprise one-way "duckbill" valves. Further, in various embodiments, as illustrated in FIGS. 15A-15B, a ball check valve 60 may be utilized as a one-way valve. Other valves may be utilized to appropriately control the flow of fluid without departing from the scope of the present invention. As illustrated in FIGS. 8-10, various embodiments include one-way valves 31, 33 that are disposed in the reservoirs 30, 32. In other embodiments, the valves may be disposed in the pumping chamber 40 and/or in the tubing 47, 48.

As noted above, in various embodiments, the reservoirs 30, 32 are made of a compliant material to allow the reservoirs 30, 32 to advantageously expand to induce a feeling of satiety in the patient. A release mechanism and/or valve 34, 35 may be disposed in the reservoirs 30, 32 to allow the reservoirs 30, 32 to expand to a certain size and/or pressure. But, once the desired size/pressure is reached, fluid is released from the reservoirs 30, 32 through the release mechanisms/valves 34, 35 to prevent over-inflation. The fluid is released from the release valves 34, 35 back to the stomach where the fluid may then be drawn in by the pumping chamber 40 or otherwise utilized by the patient's body.

In an embodiment, a flow restrictor 34, 35 may be used as a release mechanism, such that fluid will start to exit the reservoirs 30, 32 at a desired rate once the reservoirs 30, 32 have reached a predetermined size/pressure. Thus, once pumping from the pumping chamber 40 ceases, the size/pressure of the reservoirs 30, 32 will gradually reduce to a nominal size/pressure.

Figure 11A:
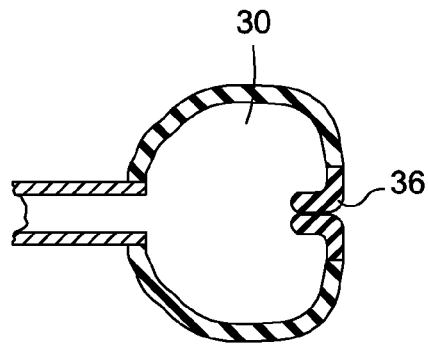
FIGS. 11A-11C illustrate sectional views of a reservoir with a burp valve in accordance with an embodiment of the present application.
Figure 11B:
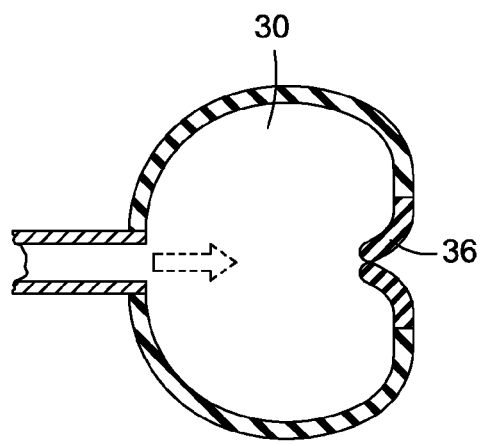
Figure 11C:
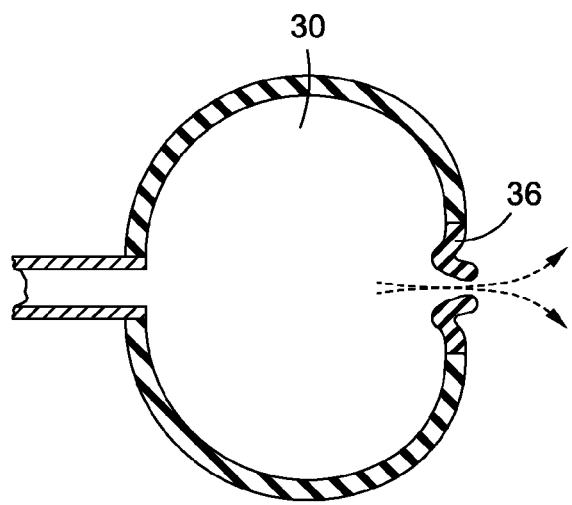
Figure 14A:
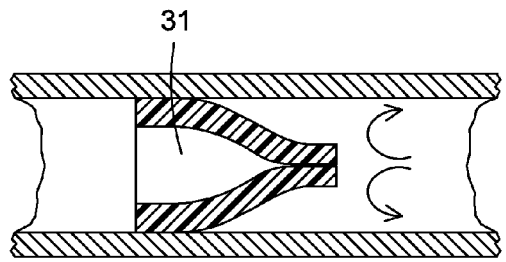
FIGS. 14A-14B illustrate sectional views of a one-way duckbill valve for use in implants of the present application.
Figure 14B:
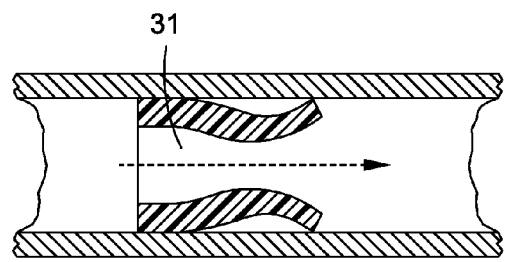

With reference to FIGS. 11A-11C, in an embodiment, a burst or burp valve 36 may be utilized as a release mechanism. For example, the burp valve 36 may be configured to open when the reservoir 30 has been stretched to a certain degree, or when a specific strain has been induced in the reservoir 30. In this manner, once the burp valve 36 opens, it may remain open until the reservoir 30 returns to a nominal size/pressure. Other release mechanisms such as pressure relief valves which crack or open at a certain pressure may similarly be used to regulate the size of the reservoir 30 or the amount of fluid in the reservoir 30.

With reference now to FIGS. 12-13, the pumping chamber 40 may be advantageously configured to be biased toward an open/expanded state. For example, the pumping chamber 40 may want to return to its largest state after the peristaltic motions 45 cease and the stomach S relaxes.

In an embodiment, as illustrated in FIGS. 12A-12B, a supporting structure, such as a chamber tube 50 may be disposed within the pumping chamber 40 to cause the pumping chamber 40 to return to its expanded state after the peristaltic motions 45 cease. A plurality of chamber tube holes 52 may be disposed in the chamber tube 50 to allow the stomach fluids to enter the chamber tube 50 and then pass through the tubes 47, 48 coupled to the reservoirs 30, 32 (see, e.g., FIGS. 8-10) during the pumping process.

In another embodiment, and with reference to FIGS. 13A-13B, an open-celled foam 56 may be disposed within the pumping chamber 40 to facilitate returning the pumping chamber 40 to its expanded state after pumping (e.g., after the peristaltic motions 45 cease). In such an embodiment, the tube 47 may be directly coupled to the pumping chamber 40, and the chamber tube 50 may not be utilized. However, a chamber tube 50 may be employed in conjunction with the open-celled foam 56. In other embodiments, the walls of the pumping chamber 40 may be sufficiently thick that they will cause the pumping chamber 40 to be biased toward its expanded state without the use of the open-celled foam 56 or the chamber tube 50. It should be understood that various combinations of these and other components may be utilized to cause the pumping chamber 40 to return to its expanded state after the peristaltic motions 45 cease.

Figure 16:
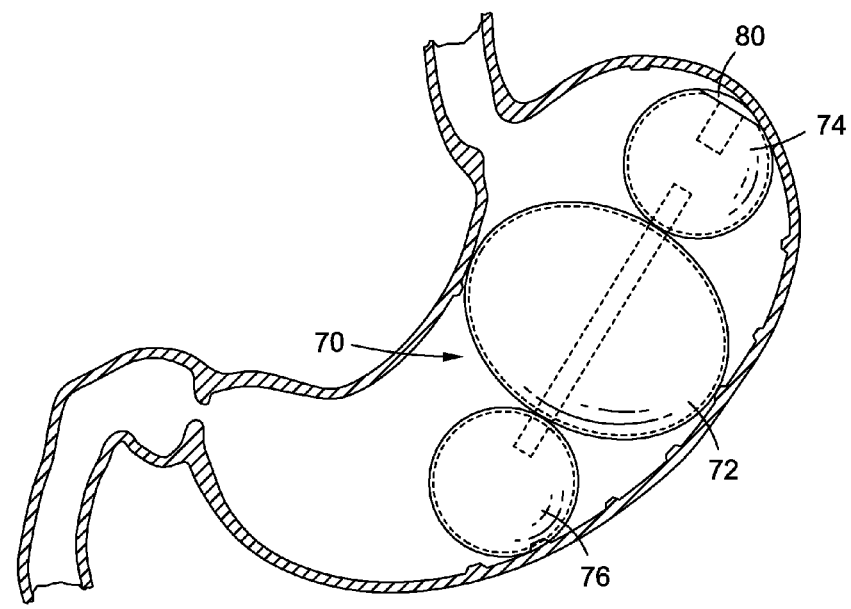
FIG. 16 illustrates an alternative tri-balloon intragastric obesity treatment implant of the present application implanted in a stomach.
Figure 17A:
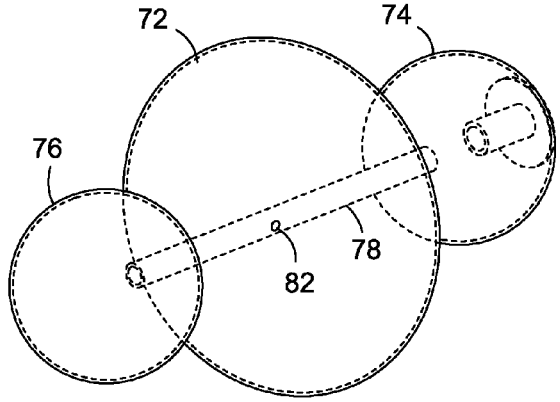
FIGS. 17A-17B illustrate details of the tri-balloon intragastric obesity treatment implant of FIG. 16
Figure 17B:
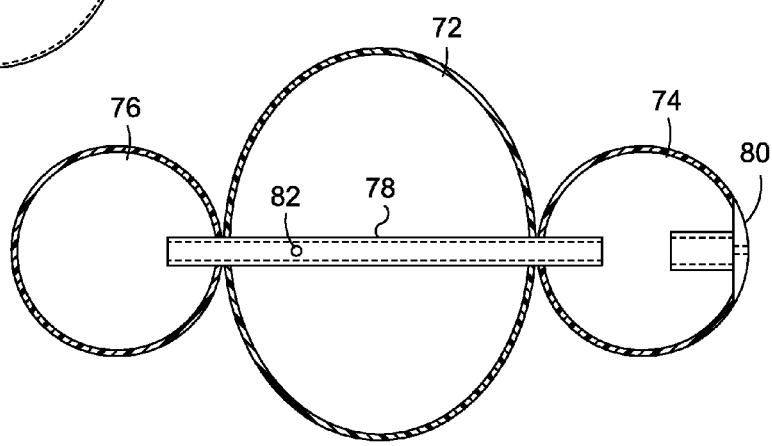

FIG. 16 illustrates an alternative tri-balloon intragastric obesity treatment implant 70 implanted in a stomach, while FIGS. 17A-17B illustrate details of the implant. The implant 70 comprises a system of three balloons; a larger central balloon 72, a smaller upper end balloon 74, and a smaller lower end balloon 76. The three balloons 72, 74, 76 are coupled together via a tubular communication channel 78. The larger central balloon 72 preferably has a fixed volume, while the two end balloons 74, 76 transfer fluid through the communication channel 78. The upper end balloon 74 further includes a fill valve 80 which is used to inflate the two end balloons. Although not shown, a fill valve is also provided for the central fixed volume balloon 72.

The larger central balloon 72 occupies space in the stomach and presses against the stomach walls to properly position the end balloons 74, 76. Desirably, the smaller upper end balloon 74 maintains contact with the cardia region for stimulation. Fluid transfer between the two end balloon 74, 76 occurs at a rate driven by the size of the communication channel 78. A relief valve 82 on the communication channel 78 and within the chamber of the central balloon 72 ensures that the end balloon 74, 76 do not break under excessive pressure.

The three balloons 72, 74, 76 are shown as generally spherical, although modifications to spheres are contemplated. Indeed, the central balloon 72 shown as slightly offset with a prolate spheroid shape. The central balloon 72 is desirably wider about its equatorial diameter than the dimension along the axis defined by the communication channel 78.

Active Balloon Reservoirs

In accordance with further embodiments of the present invention, and with reference to FIGS. 18 and 19A/19B, an intragastric obesity treatment implant 100 with fluidly-connected active balloon reservoirs comprises a gastrointestinal implant with two lobes and/or balloon reservoirs 110, 112 that may be filled with saline, air, or other fluids. In one embodiment, the balloon reservoirs 110, 112 have a nominal capacity (e.g., in a post-filled, pre-expanded state) of at least approximately 400 ml of saline, preferably between about 400-600 ml of saline. The intragastric obesity treatment implant 100 is similar to the implant 400 discussed above with reference to FIGS. 1-5.

The intragastric obesity treatment implant 100 may be configured to be implanted in the patient's stomach S, transorally, without invasive surgery, and without associated patient risks of invasive surgery. Recovery time is minimal because of reduced tissue healing post implantation. In one embodiment, the implant 100 has a product life span in the stomach S of up to one year or longer. As will be discussed, the implant 100 facilitates weight loss and obesity treatment through adipose trimming and/or fat reduction due to the patient consuming less food.

The intragastric obesity treatment implant 100 comprises the balloon reservoirs 110, 112 which are configured to occupy space inside the stomach S, thereby decreasing the amount of food that is ingestible by the patient, which may result in weight loss. The implant 100 is configured to span the upper and lower stomach regions, ranging from the antrum to the cardia.

In addition to occupying space in the stomach S, the intragastric obesity treatment implant 100 actively facilitates obesity treatment through early inducement of feelings of satiety and resulting reduced food consumption. For example, in one embodiment, a fluid disposed in the balloon reservoirs 110, 112 may move between the reservoirs via a dual-lumen connecting tether 114 that couples the upper reservoir 110 to the lower reservoir 112. As seen in FIG. 19B, the connecting tether 114 comprises a small fluid transfer passageway 116 that allows the fluid to pass between the reservoirs 110, 112.

After ingestion of food by the patient, peristaltic digestive "churning" of the stomach S begins. These peristaltic motions cause various portions of the stomach S to repeatedly contract and relax to move food through the stomach S. Based on the geometry of the stomach S and the intragastric obesity treatment implant 100, the peristaltic motions near the lower reservoir 112 (disposed near the antrum) may cause the stomach S to squeeze the reservoir. As the lower reservoir 112 is squeezed, fluid passes from it, through the fluid transfer passageway 116, and into the upper reservoir 110 (disposed adjacent the cardia). The upper reservoir 110 preferably comprises a compliant material, such that the increased amount of fluid in the reservoir 110 causes it to expand and exert increased pressure on the cardia. This increased pressure on the cardia may induce early feelings of satiety by triggering the brain to release satiety-inducing hormones, so eating will likely cease, thus promoting weight loss over time.

In accordance with various embodiments, after digestion, the peristaltic motions in the stomach cease, resulting in reduced pressure exerted on the lower reservoir 112. This reduced pressure exerted on the lower reservoir 112, in conjunction with the increased pressure in the upper reservoir 110 from the increased amount of fluid therein (and due to forces induced in the expanded compliant material in the reservoir 110 from expansion), causes the fluid in the upper reservoir 110 to return to the lower reservoir 112 via the fluid transfer passageway 116 until the pressure is substantially equalized between the two reservoirs.

As fluid transfers between the reservoirs 110, 112, the overall geometry of the implant 100 alters to encourage a varied stimulus on the stomach. Changing the character of the stimulus on the stomach walls is believed not only to encourage feelings of satiety, but also to help prevent the stomach muscles from "learning" a particular stimulus and adapting to it.

The system desirably delays return flow from the upper reservoir 110 to the lower reservoir 112 to maintain an expanded size of the upper reservoir 110 for a longer period of time. For example, the fluid transfer passageway 116 in the connecting tether 114 may be advantageously configured to have a small diameter to allow for a desired low flow rate. In one embodiment, the passageway 116 has a diameter of approximately one millimeter. In another embodiment, a center band (not shown) (e.g., a rubber band) disposed around the connecting tether 114 appropriately reduces the size of the passageway 116 to allow for a desired low flow rate. Other devices such as valves, flow restrictors, pressure reducers and the like and combinations thereof may be utilized to allow for a desired flow rate between the reservoirs 110, 112. One desired low flow rate is between about 1-20 ml/s.

As seen in FIG. 19B, the dual-lumen tether 114 also includes a deflation lumen 118 extending between the reservoirs 110, 112, parallel to the passageway 116. The deflation lumen 118 is larger than the passageway 116, and is only accessed to evacuate fluid from the reservoirs 110, 112 during explanation. The larger deflation lumen 118 is fitted on both sides with one-way valves 120 (e.g., duck-bill valves as shown) which are oriented in opposite directions. The valves 120 prevent fluid flow from the deflation lumen 118 into each reservoir, and therefore prevent flow from one reservoir to another through the deflation lumen 118. The orientation of the valves 120 is such that they will open if a vacuum (predetermined pressure differential across the valves) is introduced through a vacuum port 122. For example, an instrument introduced trans-orally through the esophagus may be used to access the vacuum port 122 and pull fluid therefrom. The relatively large size of the deflation lumen 118 and uninhibited flow through the valves 120 encourages rapid deflation of the balloon reservoirs 110, 112 during explanation.

The tether 114 is rigid enough so that the dual lumens do not collapse or kink under various operating conditions.

However, the tether 114 remains flexible enough such that the device as a whole can roughly orient itself inside a variety of stomach geometries. Indeed, the intragastric obesity treatment implant 100 in one embodiment is symmetric across the balloon reservoirs 110, 112 and may completely invert so that the reservoir 112 is now the upper reservoir. One solution is to provide a reinforcing coil embedded within a more flexible tether 114. The tether 114 and all of its integral components may be manufactured from materials including, but not limited to, rubbers, fluorosilicones, fluoroelastomers, thermoplastic elastomers, or any combinations thereof, while a reinforcing coil may be formed of those materials as well as flexible metals such as Nitinol.

Figure 20:
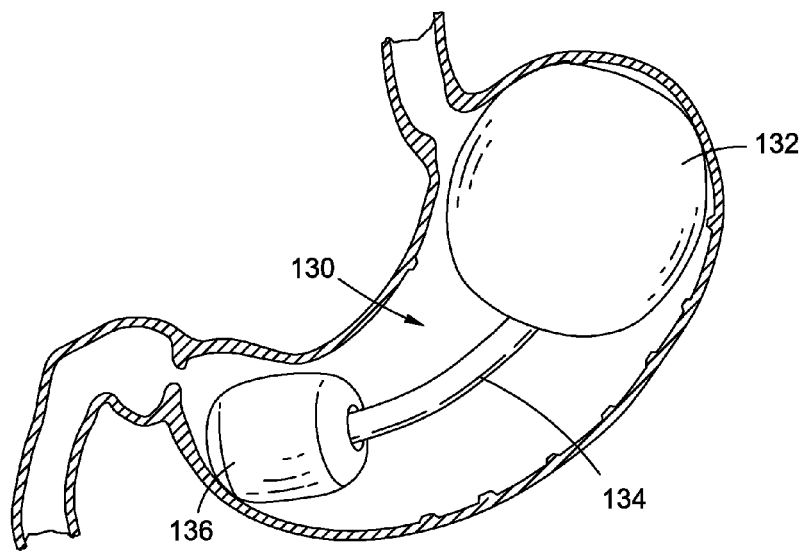
FIG. 20 shows an alternative dual-balloon intragastric obesity treatment implant with two inflated and fluidly-connected balloons in a patient's stomach.
Figure 21A:
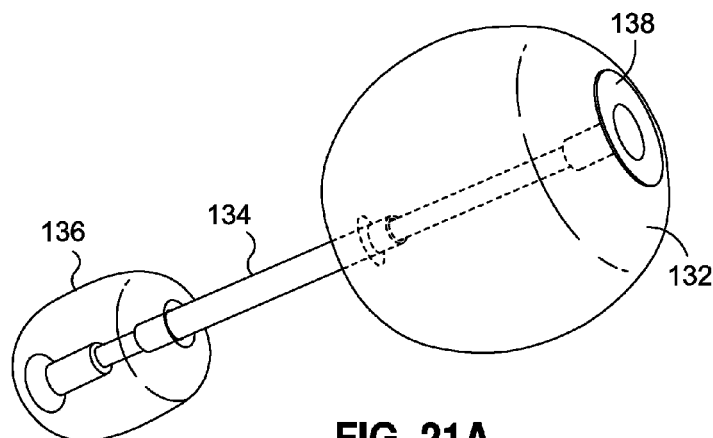
FIGS. 21A-21B illustrate details of the dual-balloon intragastric obesity treatment implant as in FIG. 20.
Figure 21B:
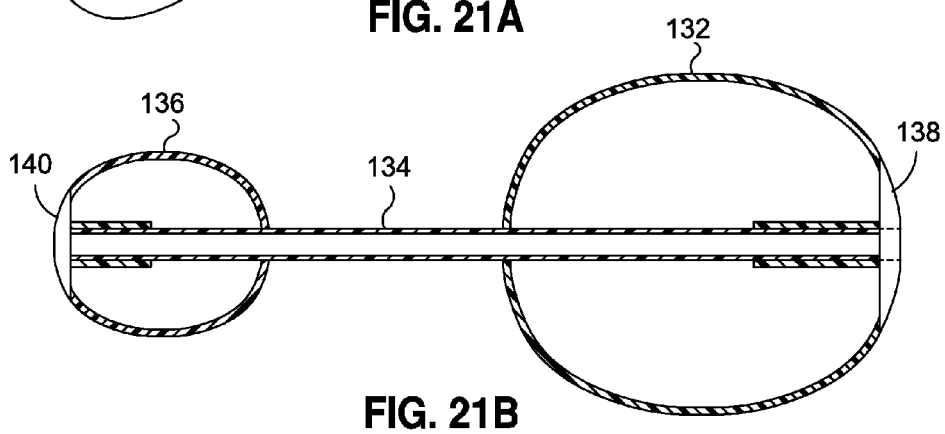

FIG. 20 shows another dual-balloon intragastric obesity treatment implant 130 with a larger upper cardia-stimulating balloon 132 fluidly-connected via relatively stiff tube 134 to a smaller positioning balloon 136. With reference also to FIGS. 21A-21B, the tube 134 includes a plurality of apertures (not shown) along its length within each of the balloons 132, 136. Each of the balloons 132, 136 has a one-way fill valve 138, 140, respectively, so that both balloons may be filled from either valve. Alternatively, only one of the balloons 132, 136 has a fill valve. Fluid may transfer between the balloons 132, 136 from stomach churning, though the rate of return to equilibrium will be slower and depend on the size of the interconnecting flow apertures. Preferably the rate of return flow is about half the maximum rate of forward flow, which is induced by the stomach squeezing on one or the other balloon.

The larger balloon 132 has an inflated volume at least twice as big, and preferably at least three times as big, as the smaller balloon 136 and is shaped to conform to the relatively larger cardia region within the stomach. The smaller balloon 136 has an inflated size large enough to prevent passing through the pylorus, but large enough to provide an atraumatic surface in contact with the antrum region in the lower region of the stomach. The stiff tube 134 ensures that the larger balloon 132 maintains contact with the cardia, stimulating upper baroreceptors.

Figure 22A:
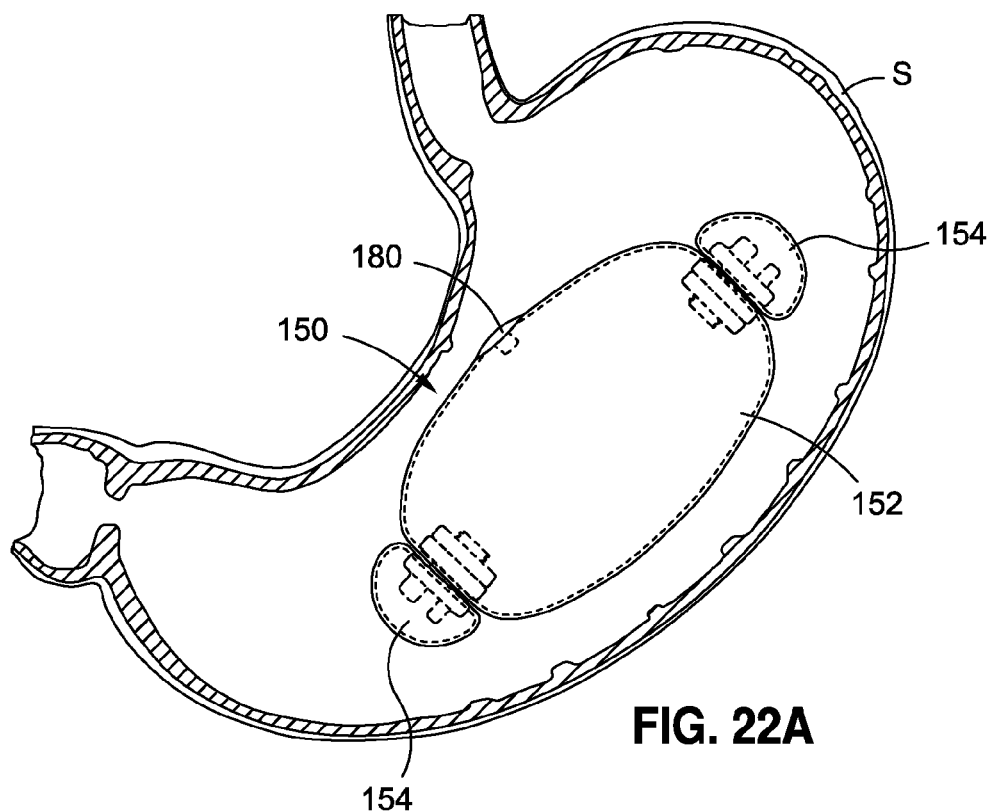
FIG. 22A illustrates a side view of an intragastric obesity treatment implant with an inflated pumping chamber fluidly-connected to two reservoirs on opposite ends in a patient's stomach in accordance with an embodiment of the present application.
Figure 22B:
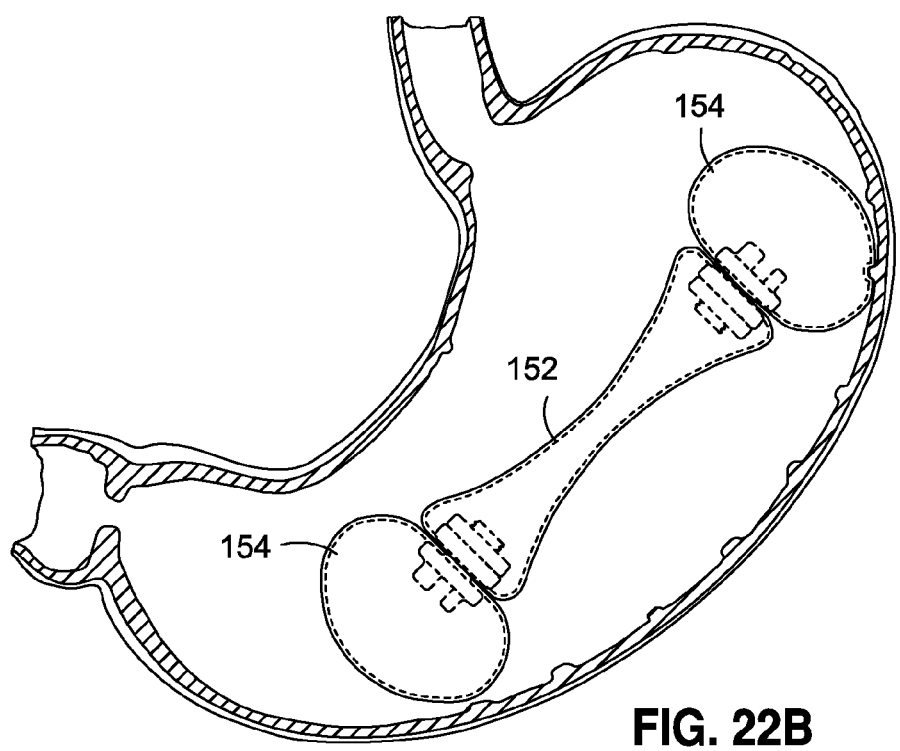
FIG. 22B illustrates a side view of the intragastric obesity treatment implant in FIG. 22A with the pumping chamber being compressed by a patient's stomach to fill the two reservoirs.

FIGS. 22A and 22B show an intragastric obesity treatment implant 150 in a patient's stomach S in two different configurations. The implant 150 comprises a large central pumping chamber 152 fluidly connected between two smaller reservoirs 154 on either end. In FIG. 22A the central pumping chamber 152 is expanded to fill a substantial portion of the interior of the stomach S, while in FIG. 22B the pumping chamber has been compressed such that an outside fluid is transferred to the end reservoirs 154. In one embodiment, the pumping chamber 152 has a capacity of at least about 400 ml of saline, preferably between about 400-600 ml of saline, while the combined capacity of the smaller reservoirs 154 is also at least about 400 ml. The intragastric obesity treatment implant 150 is similar in many respects to the implant 28 discussed above with reference to FIGS. 8-10, where, however, in contrast, a pumping chamber 40 moves stomach fluids or juices between stimulation reservoirs 30.

Figure 23:
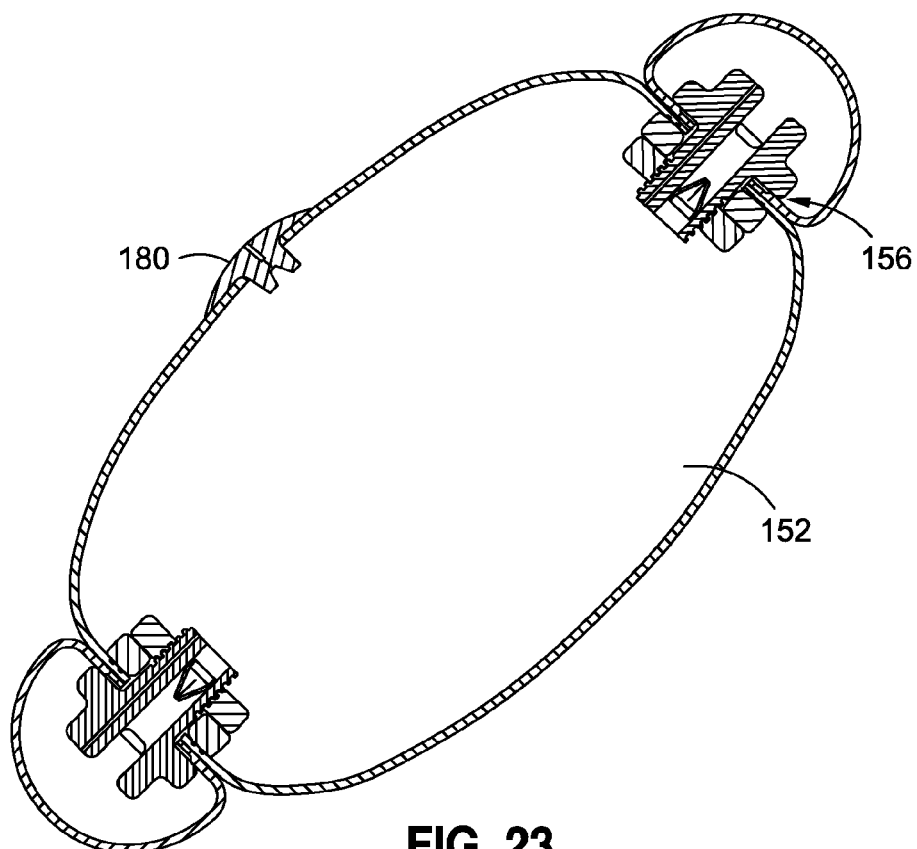
FIG. 23 is a sectional view of the intragastric obesity treatment implant in FIG. 22A showing one-way valves and flow restrictors between the pumping chamber and two reservoirs.
Figure 24:
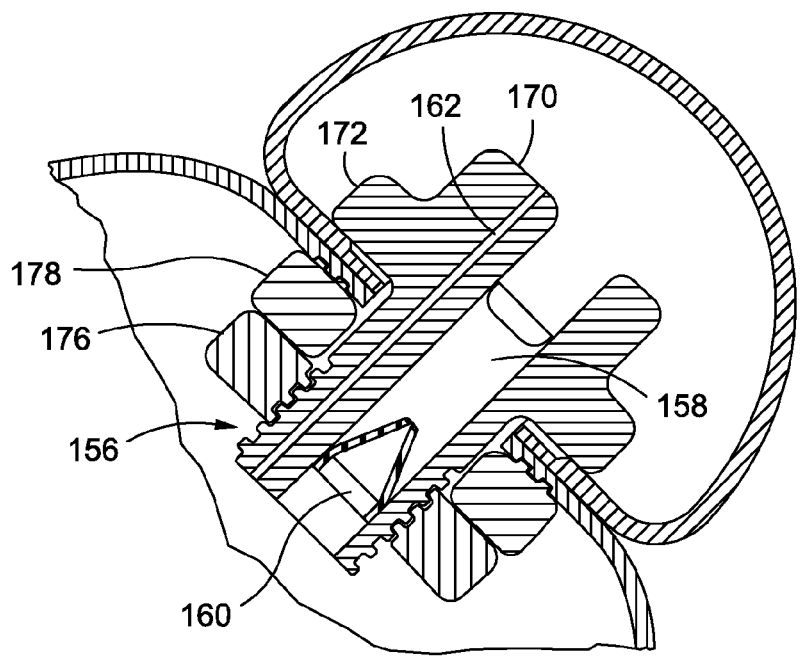
FIG. 24 is a detailed sectional view of a one-way valve and flow restrictor between the pumping chamber and one of the two reservoirs in the intragastric obesity treatment implant of FIG. 22A.

FIGS. 23 and 24 illustrate internal components of the intragastric obesity treatment implant 150, specifically between the pumping chamber 152 and the reservoirs 154 on either end. As seen in the detail of FIG. 24, a connector 156 between the chamber 152 and each reservoir 154 includes a large flow lumen 158 housing a one-way valve 160, and a smaller lumen 162 acting as a fluid transfer channel and providing flow restriction between the pumping chamber and each reservoir. The connector 156 comprises a substantially tubular male member 170 within which is formed the lumens 158, 162, and which has a radially outward-directed flange 172 that contacts an interior wall of the respective end reservoir 154. A portion of the tubular male member 170 extending within the interior of the pumping chamber 152 includes external threading for mating with internal threading on a nut 176. The nut 176 tightens along the male member 170 and forces a washer 178 against an interior wall of the pumping chamber 152. Both the washer 178 and the flange 172 of the male member 170 include concentric circular ribs that engage across the walls of the pumping chamber 152 and reservoir 154 and help prevent slipping of the assembly.

Desirably, the portion of the male member 170 within the end reservoirs 154 is shaped to allow for easy handling, and in particular for applying torque, through a deflated end reservoir 154. For instance, the male member 170 within the end reservoirs 154 has a hexagonal, square or winged shape. An aperture in the side wall of the pumping chamber 152 that receives a fill valve 180 permits introduction of the nuts 176 and washers 178, and also provides access for a tool for either holding or turning the nut during assembly.

Once situated within the stomach S, the physician inflates the implant 150 through the valve 180 located along one side of the central pumping chamber 152. After food is ingested, the stomach's peristaltic forces act on the larger pumping chamber 152 and squeeze fluid through the fluid transfer lumens 162 of the connectors 156, and into the end reservoirs 154, as depicted in FIG. 22B. The end reservoirs 154 thus inflate and stimulate the stomach walls. The increased pressure within the inflated end reservoirs 154 creates a pressure differential across the connector 156, thus initiating a return flow from each reservoir back to the central pumping chamber 152. Additionally, an open-celled foam (such as that shown in FIGS. 13A-13B) may be disposed within the pumping chamber 152 to facilitate returning it to its expanded state after pumping (e.g., after the peristaltic motions cease). In other embodiments, the walls of the pumping chamber 152 may be sufficiently thick that they will cause it to be biased toward its expanded state without the use of the open-celled foam. It should be understood that various combinations of these and other components may be utilized to cause the pumping chamber 152 to return to its expanded state after the peristaltic motions cease.

Because of the relatively small size of the fluid transfer lumens 162, reverse flow of fluid from the end reservoirs 154 to the central pumping chamber 152 takes an extended period of time, preferably greater than two minutes and potentially up to several (e.g., two) hours. One desired low flow rate is about 1-20 ml/s. Preferably, a single set of stomach contractions are sufficient to create the geometry shown in FIG. 22B, which is believed to stimulate the inner walls of the stomach and induce satiety more than the relaxed geometry of FIG. 22A.

Dual Balloon Reservoirs

Figure 25A:
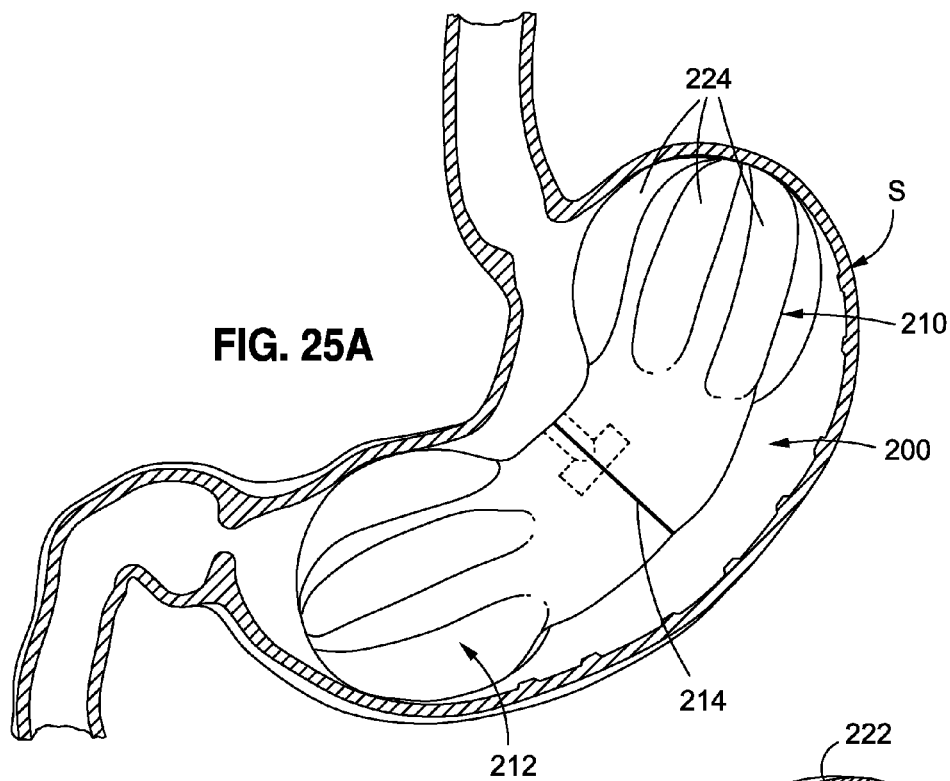
FIGS. 25A-25B illustrate an alternative intragastric obesity treatment implant positioned within a patient's stomach and in sectional view, the intragastric obesity treatment implant having dual connected balloons in a dog bone configuration with a partition and fluid transfer therebetween.
Figure 25B:
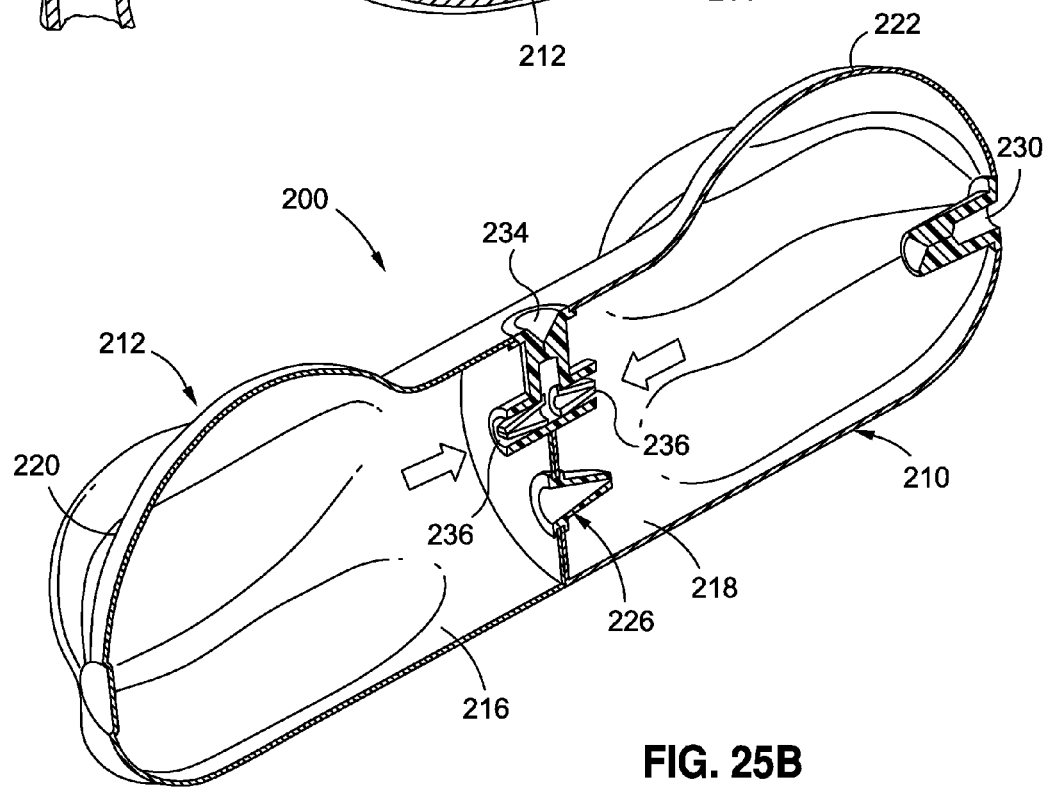

In accordance with further embodiments of the present invention, and with reference to FIGS. 25A-25B, an intragastric obesity treatment implant 200, such as a dual balloon gastrointestinal implant includes two lobes and/or balloons 210, 212, that may be filled with saline, air, or other fluids. In a preferred embodiment, the balloons 210, 212 have a nominal capacity (e.g., in a post-filled, pre-expanded state) of at least approximately 400 g, or about 400 ml, of saline. For example, the combined fluid capacity of the balloons 210, 212 may be between about 400-700 ml of saline, with a more preferred capacity of about 500 or 600 ml. In the illustrated embodiment, the inflated intragastric obesity treatment implant 200 describes a somewhat dog-bone shape, with identical lower and upper balloons 210, 212 having enlarged, fluted outer ends joined by a smaller, generally cylindrical middle portion. The middle portion of the implant 200 is strengthened to prevent kinking by virtue of its relative size and a central partition, as will be explained. The implant 200 is configured to span the upper and lower stomach regions, as shown in FIG. 25A, with the lower balloon 210 adjacent the antrum and the upper balloon 212 adjacent the cardia.

The balloons 210, 212 are desirably separately formed and joined to each other. More particularly, the intragastric obesity treatment implant 200 comprises two identical balloons 210, 212 generally aligned along a longitudinal axis and bonded together along a centrally located diametrically-oriented partition 214. As seen in FIG. 25B, the partition 214 desirably comprises the juxtaposed flat inner end walls of the two balloons 210, 212. From the inner end wall outward, each balloon 210, 212 has a tubular portion 216, 218 that extends along the longitudinal axis and widens at bulbous end portions 220, 222. Desirably, the end portions 220, 222 feature a series of longitudinal flutes or ridges 224 around their circumference between which are grooves, best seen in FIG. 25A.

As will be discussed, the intragastric obesity treatment implant 200 facilitates weight loss and obesity treatment by taking up space within the stomach as well as by stimulating satiety-inducing nerves. The implant 200 occupies space inside the stomach S, thereby decreasing the amount of food that is ingestible by the patient, which may result in weight loss. The flutes or ridges 224 and accompanying grooves prevent obstruction of food as it moves through the pylorus and into the duodenum of the patient. Namely, food passes by the implant 200 through the grooves between the flutes 224 and along the stomach S walls.

The intragastric obesity treatment implant 200 further actively treats obesity through early inducement of feelings of satiety and resulting reduced food consumption. For example, in one embodiment, fluid such as saline may move between the balloons 210, 212 across the center partition 214 (FIG. 25B) that separates the inner chambers of the balloons 210, 212. The center partition 214 includes a duckbill valve 226 and parallel fluid passageways (not shown) that allow fluid to pass between the balloons 210, 212. In a preferred embodiment, the duckbill valve 226 permits fluid to flow from the lower balloon 210 to the upper balloon 212 but prevents a reverse flow. One or more fluid passageways near or surrounding the valve 226 permit fluid flow back from the upper balloon 212 to the lower balloon 210. The flow orifice through the duckbill valve 226 is larger than the combined area of the return passageway(s), and thus fluid may flow at a greater rate from the lower balloon 210 to the upper balloon 212.

After ingestion of food by the patient, random peristaltic digestive "churning" of the stomach S begins. These peristaltic motions cause various portions of the stomach S to repeatedly contract and relax to move food through the stomach S. Based on the geometry of the stomach S and the intragastric obesity treatment implant 200, the peristaltic motions near the lower balloon 212 (disposed near the antrum) may cause the stomach S to squeeze the balloon 212. As the lower balloon 212 is squeezed, fluid passes rapidly through the valve 226 in the center partition 214, and into the upper balloon 210 (disposed adjacent the cardia). The upper balloon 210 desirably comprises a compliant material, such that the increased amount of fluid in the balloon 210 causes the balloon 210 to expand and exert increased pressure on the cardia. This increased pressure on the cardia may induce early feelings of satiety by triggering the brain to release satiety-inducing hormones, so eating will likely cease, thus contributing to eventual weight loss.

In accordance with various embodiments, after digestion, the peristaltic motions in the stomach cease, resulting in reduced pressure exerted on the lower balloon 212. This reduced pressure, in conjunction with the increased pressure in the upper balloon 210 from the increased amount of fluid therein (and due to forces induced in the expanded compliant material in the balloon 210 from expansion), causes the fluid to return to the lower balloon 212 via the fluid passageway(s) in the center partition 214 until the pressure is substantially equalized between the two balloons 210, 212.

The return flow to the lower balloon 212 may be inhibited to maintain an expanded size of the upper balloon 210 for a longer period of time. For example, the passageway(s) in the center partition 214 preferably has a maximum size to allow for a desired low flow rate. In one embodiment, the passageway may be a through hole having a diameter of approximately 1 mm. Stated another way, the maximum flow rate from the lower balloon 212 to the upper balloon 210 is desirably substantially greater than in the reverse direction. For example, the duckbill valve 226 enables twice the flow rate from the lower balloon 212 to the upper balloon 210 than the reverse flow through the return passageway(s). In one specific example, the entire intragastric obesity treatment implant 200 has a fluid capacity of about 500 ml which is typically split evenly (250-250) between the two balloon chambers when the pressures in both are equal. Up to 200 ml of the fluid in the lower balloon 212 chamber rapidly flows through the valve 226 to the upper balloon 210 chamber from peristaltic contractions. This may take just a few seconds. Swelling of the upper balloon 210 applies pressure to the surrounding cardia and its subcutaneous nerves, thereby stimulating the brain's release of satiety-inducing hormones. Subsequently, the return fluid passageway(s) permit a trickle flow back to the lower balloon 212 chamber that takes at least 10 seconds, potentially minutes.

The intragastric obesity treatment implant 200 is preferably implanted in the patient's stomach S transorally, without invasive surgery and its associated patient risks. Recovery time is minimized because of reduced tissue healing post implantation. In one embodiment, the implant 200 may have a product life span in the stomach S of up to one year or longer. The upper balloon 212 conveniently has a fill valve 230 along the longitudinal axis at the bulbous end 222 to allow the implant 210 to be filled with saline after implantation in the stomach S. By filling the upper balloon 212, such as by using a fill line pre-connected to a syringe, the lower balloon 210 is also filled by transfer through the fluid passageway(s) across the partition 214. Thus, the implant 200 may be disposed in the stomach S via the esophagus in a substantially non-inflated state. For example, a lubricated (e.g., Teflon), thin-walled tube (not shown) may be inserted through the patient's mouth, down the esophagus, and partially into the stomach S. The implant 200 is preloaded in a non-inflated and compressed state into the tube prior to insertion, and then expelled into the stomach S from the distal end of the tube. A fluid filling tube coupled to the fill valve 230 is removably coupled to the intragastric obesity treatment implant 200 prior to insertion through the lubricated tube to facilitate filling the implant after implantation. The fill valve 230 is a one way valve such that the filling tube can be removed after inflation of the implant 200 without a substantial amount of fluid being lost.

In a preferred embodiment, the intragastric obesity treatment implant 200 features a rapid deflation valve 232 located approximately at the center of the implant which can deflate both chambers of the balloons 210, 212 simultaneously. Specifically, the valve 232 has a T-shaped configuration with a nipple 234 opening to the exterior of the implant and in fluid communication with a pair of one-way valves 236 extending in opposite directions into each of the dual fluid chambers of the implant. The one-way valves 236 permit flow from the dual chambers and out of the nipple 234, but prevent flow in the opposite direction. At the time that the implant will be removed, a "lasso" device (not shown) with a slip-knotted cord is used to capture the intragastric obesity treatment implant 200 about its midsection. The sideways-oriented nipple 234 may then be accessed using a wire-stiffened fluid removal line or aspirator having an end specially configured to engage the nipple (e.g., with a single-barbed end). Once engaged, the fluid removal line exerts a vacuum pressure on the two one-way valves 236 to evacuate the inside of both balloon chambers simultaneously. The vacuum may be created using an empty syringe connected to the fluid line.

Alternatively, a standard endoluminal cutter maybe deployed down an overtube through the esophagus to cut each balloon chamber in one or more places so the saline therein can drain into the stomach cavity. Once the balloons 210, 212 collapse, the entire implant can be refracted into the overtube using a standard grabber after withdrawal of the cutter. The intragastric obesity treatment implant 200 may be configured to be removed in other ways, for example, by passing out of the patient through digestion.

Figure 26A:
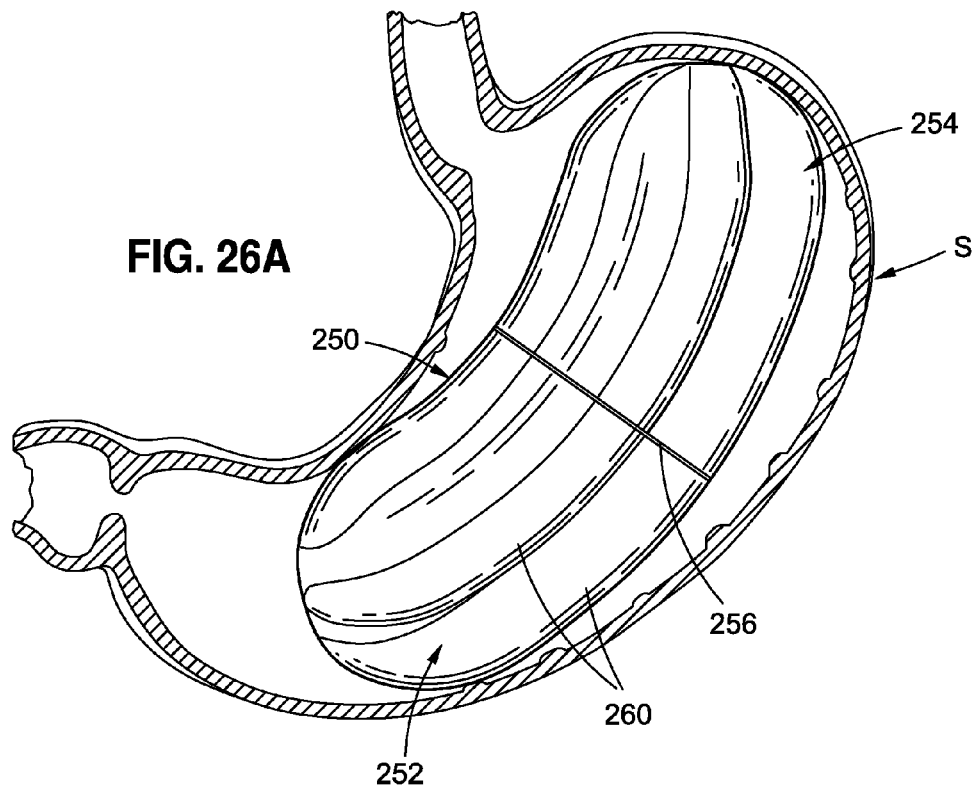

FIG. 26A shows an alternative dual-balloon intragastric obesity treatment implant 250 similar to that in FIGS. 25A-25B but with a more uniform longitudinal shape. Specifically, the implant 250 includes a lower balloon 252 connected to an upper balloon 254 at a central diametric partition 256. The two balloons 252, 254 are connected at their inner ends and each feature longitudinal flutes 260 which match up to provide uniform longitudinal flutes and intermediate grooves along the entire length of the implant 250. Although not shown, the implant 250 desirably features a fill valve on one end, a one-way fluid transfer valve as well as return fluid passageways in the partition 256, and a rapid deflation valve, like the embodiment of FIGS. 25A-25B.

Figure 26B:
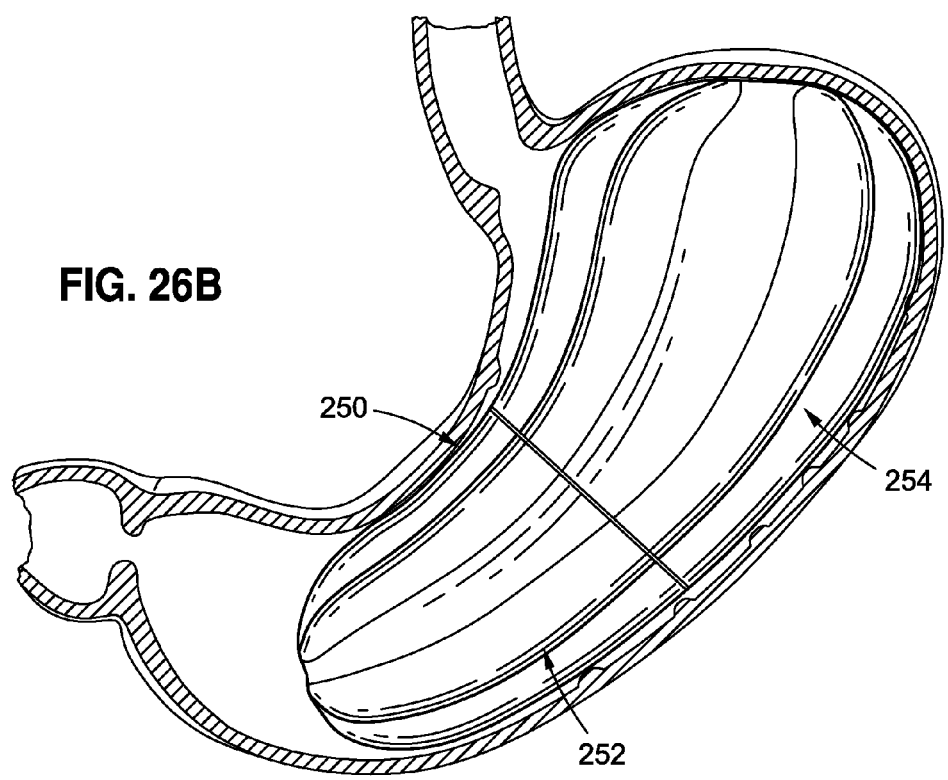
FIG. 26B illustrates contraction of the stomach walls to squeeze fluid from a lower balloon to an upper balloon.

Once implanted in the stomach S, peristaltic contractions may squeeze the lower balloon 252 as shown in FIG. 26B. This causes fluid transfer through the one-way valve in the partition 256, which rapidly fills the upper balloon 254. The asymmetric shape created contacts the inner walls of the cardia in the upper end of the stomach and stimulates satiety-inducing nerves. Moreover, the presence of the filled intragastric obesity treatment implant 250 takes up space within the stomach S, though the deep grooves between the flutes 260 help food bypass the implant.

Concentric Chamber Gastric Implant

Figure 27:
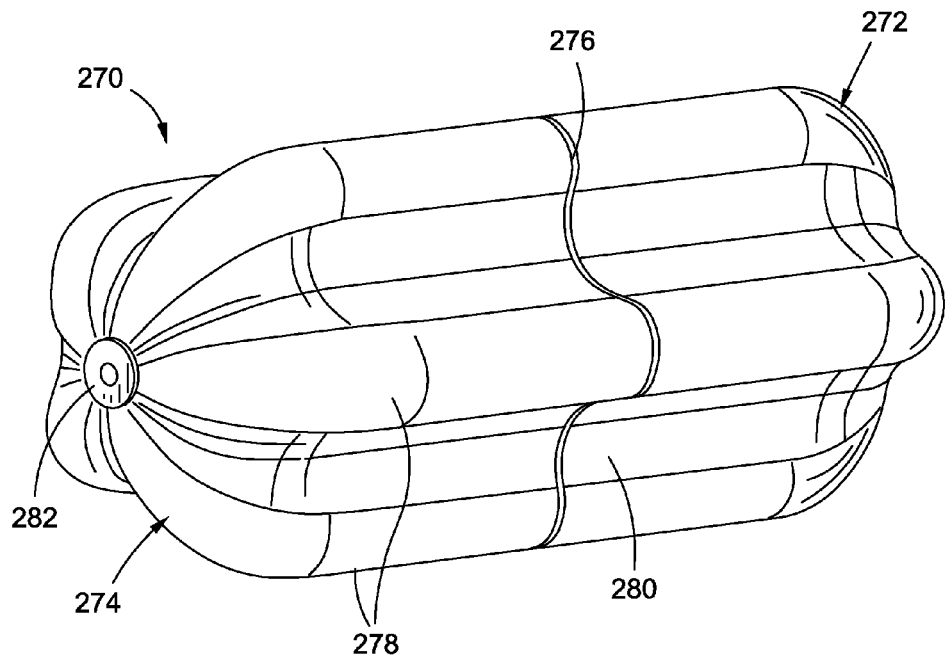
FIGS. 27-29 are various views of a concentric chamber inflatable intragastric obesity treatment implant of the present application having an outer saline-filled chamber and an inner air-filled chamber.
Figure 28:
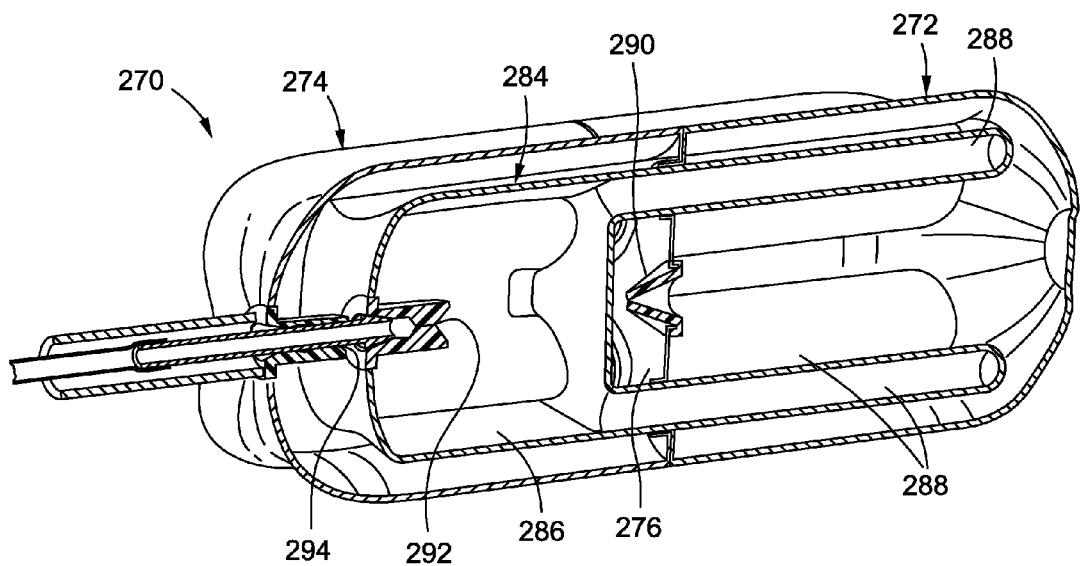

FIGS. 27-29 illustrate a still further inflatable intragastric obesity treatment implant 270 having an outer saline-filled chamber and an inner air-filled chamber. The exterior shape of the implant 270 is similar to the embodiment shown in FIGS. 26A-26B, with a first exterior balloon 272 connected at one end in series to a second identical exterior balloon 274 at a partition wall 276. The two balloons 272, 274 are oriented along a longitudinal axis and the partition wall 276 extends diametrically perpendicular to the axis. Each of the balloons 272, 274 has a rounded outer end shape with a plurality (6 shown) of longitudinal flutes 278 creating longitudinal grooves 280 therebetween. The flat mating inner ends abut at the partition plane and the alternating flutes 278 and grooves 280 line up to form the elongated somewhat oval-shaped configuration. The intragastric obesity treatment implant 270 features a convenient outer fill valve 282 centrally located on the outer end of the second balloon 274.

As seen in FIG. 27, the intragastric obesity treatment implant 270 has a configuration much like that shown in FIGS. 26A-26B, and indeed functions much like that earlier embodiment. In particular, the implant 270 may be deflated for transoral insertion into the stomach through the esophagus using a lubricated overtube, and then filled. Once in the stomach, the implant 270 takes up space and also actively changes shape in reaction to peristaltic contractions. Specifically, fluid may be transferred between the two balloons 272, 274 to enlarge one or the other. Furthermore, the outer flutes 278 contact the stomach wall and channels defined by the grooves 280 therebetween permit food to flow past the implant.

In contrast to the earlier embodiment, however, the intragastric obesity treatment implant 270 features a concentric balloon structure with dual saline-filled outer balloons surrounding an air-filled core balloon that occupies volume within the outer balloons. With reference to the longitudinal sectional view of FIG. 28, the connected outer balloons 272, 274 having the diametric partition 276 therebetween are shown surrounding an inner air-filled core balloon 284. The core balloon 284 includes an upper portion formed as a monolithic bladder 286 residing entirely within the chamber of the first outer balloon 272, and a lower portion comprising a series of elongated longitudinally-oriented bladders 288. The elongated bladders 288 are each fluidly connected to the single monolithic bladder 286 and extend across the partition 276 into the chamber of the second outer balloon 274. It should be noted that the air-filled core balloon 284 may be located within a single outer saline-filled outer balloon in a manner that orients the outer balloon, though the partitioned dual outer balloon provide additional advantages The partition 276 provides sealed apertures for passage of each of the elongated bladders 288 without compromising the fluid separation between the chambers of the first and second outer balloons 272, 274. The partition 276 includes a duckbill valve 290 and parallel fluid passageways (not shown) that allow fluid to pass back and forth between the balloons 272, 274. In a preferred embodiment, the duckbill valve 290 permits fluid to flow from the first or lower balloon 272 to the second or upper balloon 274 but prevents reverse flow. One or more fluid passageways near or surrounding the valve 290 permit fluid flow back from the second balloon 274 to the first balloon 272. The flow orifice through the duckbill valve 290 is larger than the combined area of the return passageway(s), and thus fluid may flow at a greater rate from the first balloon 272 to the second balloon 274. As before, the first outer balloon 272 desirably resides below the second outer balloon 274 in the stomach such that the outer fill valve 282 is located on the proximal end (or toward the esophagus) of the intragastric obesity treatment implant 270.

With reference still to FIG. 28, the outer fill valve 282 has an outlet aperture 294 projecting into the second outer balloon 274 and toward an inner fill valve in the corresponding end of the core balloon 284. As will be described below, a single fill tube may be used to inflate both the inner core balloon 284 with air, and the outer dual balloons 272, 274 with saline.

The core balloon 284 has a single fluidly-connected chamber and remains filled with air throughout use of the implant. In contrast, the two outer balloons 272, 274 transfer fluid across the partition 276 over the implant duration, as was described above. More particularly, fluid rapidly passes through the one-way valve 290 from the chamber of the first outer balloon 272 to the chamber of the second outer balloon 274, and then returns more slowly through the surrounding fluid passageway(s). Since the monolithic bladder 286 of the upper portion has a larger volume than the combined volumes of the elongated bladders 288 of the lower portion of the air-filled balloon 284, the intragastric obesity treatment implant 270 has greater buoyancy toward the end of the second outer balloon 274 having the fill valve 282. As a consequence, the end with the fill valve 282 remains oriented upwards toward the cardia by virtue of its greater buoyancy. Moreover, as the first outer balloon 272 tends to be squeezed more forcefully by contractions of the lower stomach at the antrum, some of the air residing in the elongated bladders 288 may be forced across the partition 276 into the chamber of the second outer balloon 274, further contributing to the buoyancy differential across the partition. All this results in the end having the second outer balloon 274 floating and remaining in the top of the stomach adjacent the cardia. Because the fill valve 282 permits more rapid fluid transfer to the chamber of the second outer balloon 274, this end tends to swell to a greater extent and contact the surrounding cardia, thus stimulating the subcutaneous nerves and contributing to a sensation of being full.

Figure 29A:
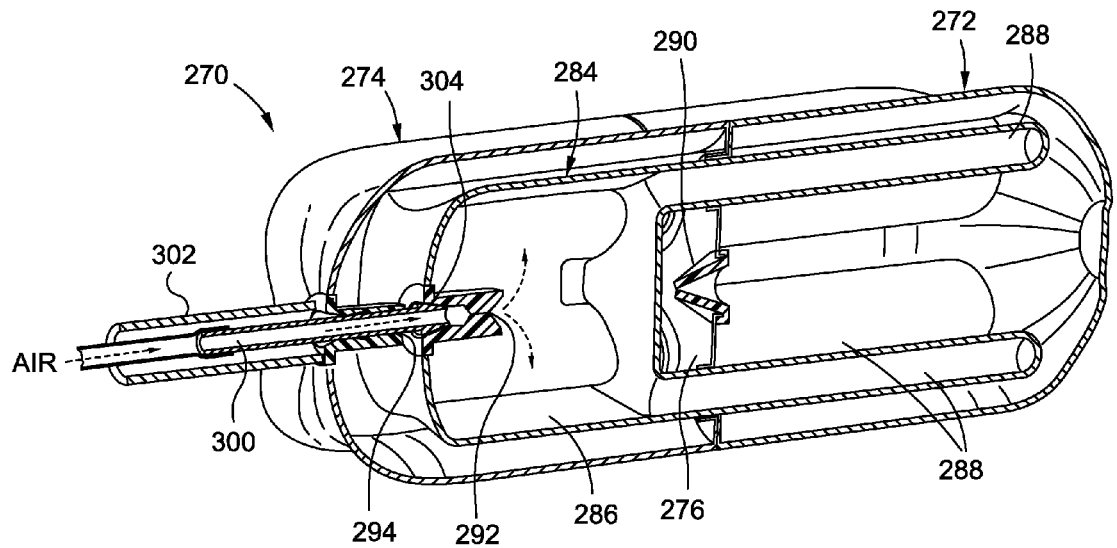
Figure 29B:
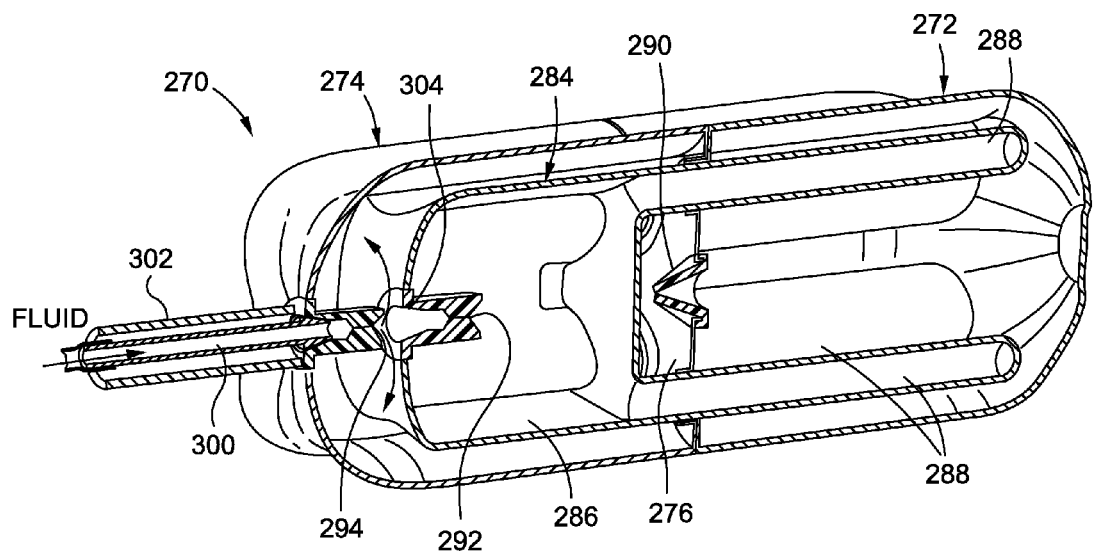

FIGS. 29A and 29B illustrate two stages in filling the intragastric obesity treatment implant 270. First, an obturator 1600 advances through an overtube 1602 that passes through the esophagus. The distal end of the obturator 1600 has a tapered shape which easily engages and penetrates a central outer opening of the fill valve 282. FIG. 29A illustrates the first, air-filling position, with the tip of the obturator 1600 engaged in the inner valve that is sealed to only the air balloon. FIG. 29B shows the obturator tube still in place, but the lumen tip is now pulled back slightly, so it "pops" into the second, (outer) valve.

The operator advances the obturator 1600 until a distal enlarged tip 1604 pops into a similarly-shaped cavity (not numbered) within the fill valve 282, as seen in FIG. 29A. In this position, the open end of the obturator 1600 lumen fluidly communicates with an outlet 292 of the inner fill valve that opens to the interior of the core balloon 284. The technician then inflates the core balloon 284 with air. Subsequently, the technician retracts the obturator 1600 a short distance into the position shown in FIG. 29B, wherein the distal enlarged tip 1604 pops into another mating cavity within the outer fill valve 282. At this location, the open end of the obturator 1600 fluidly communicates with the fill valve outlet 294 that opens to the interior of the second outer balloon 274. The technician can then fill the second outer balloon 274 with saline, which gradually migrates to the chamber of the first outer balloon 272 through the fluid passageway(s) in the partition 276. With this configuration, the concentric air/saline balloons may be filled using one fill tube in a sequential procedure.

Figure 30A:
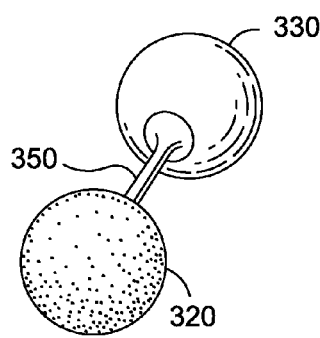
FIGS. 30A-30D illustrate perspective views of intragastric obesity treatment implants with various configurations of pumping chambers, tubing, and reservoirs in accordance with various embodiments of the present application.
Figure 30B:
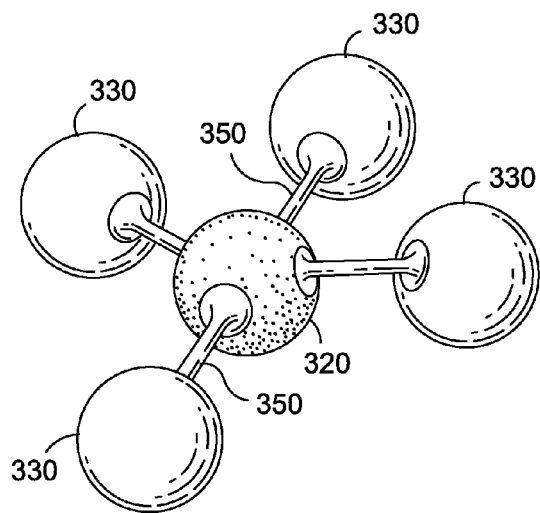
Figure 30C:
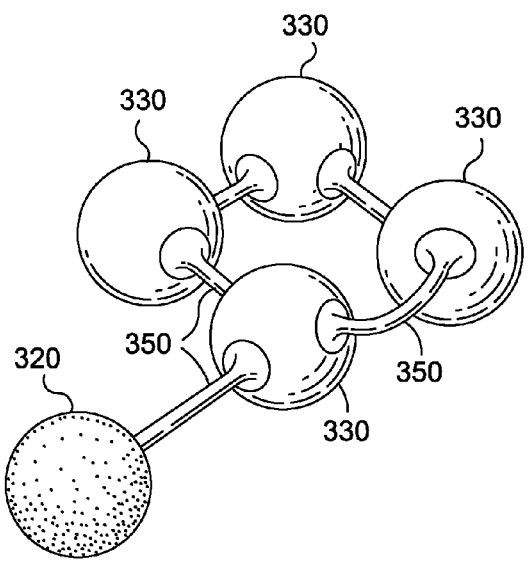
Figure 30D:
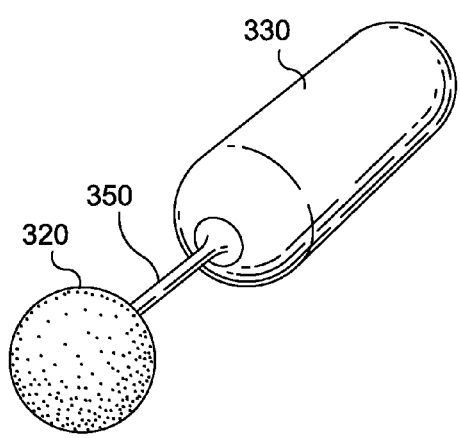

FIGS. 30A-30D schematically illustrate various configurations of reservoirs 330 in the shape of simple spheres connected by tubing 350, in series or in parallel, and with a pumping chamber 320. Various numbers and/or configurations of reservoirs 330 and tubing 350 are contemplated within the scope of the present invention. For instance, one pumping chamber 320 in series with a single reservoir 330 is shown in FIGS. 30A and 30D. One pumping chamber 320 in the middle of multiple reservoirs 330 is shown in FIG. 30B, while a pumping chamber 320 connected to one of a loop of reservoirs 330 is seen in FIG. 30C.

While not shown, the outer surface of the intragastric implants disclosed herein may further include additional uneven surface features such as small rounded bumps or protrusions, quill-like extensions, dimples or recesses, and the like. These features, upon contact with the inner stomach wall of the patient may further trigger hormone release or otherwise aid the patient in feeling full. Such features may be particularly effective for those embodiments which stimulate the cardia. The examples in FIGS. 31-33 may be applied to any of the various implants and surfaces disclosed herein.

Figure 31:
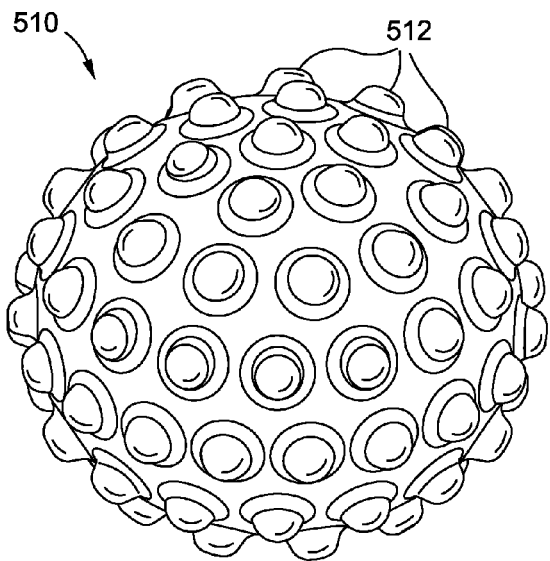
FIGS. 31-33 illustrate intragastric implant surface features that provide additional stomach cavity stimulation.

For instance, FIG. 31 illustrates a spherical intragastric implant 510 having numerous external protrusions or bumps 512 projecting outward therefrom. These bumps 512 separately contact the inner walls of the stomach, potentially increasing the stimulation to the surrounding satiety-sensing nerves. As shown, a plurality of bumps 512 may be equally spaced apart on the outer surface and interspersed with flat portions. In one embodiment, the bumps 512 may be of equal heights and diameters, or they may be configured to have different heights and/or diameters. For example, having bumps 512 with different heights and/or diameters may be advantageous for preventing the stomach from adjusting to the bumps. The bumps 512 separately contact the inner walls of the stomach, potentially increasing the stimulation to the surrounding satiety-sensing nerves.

Figure 32:
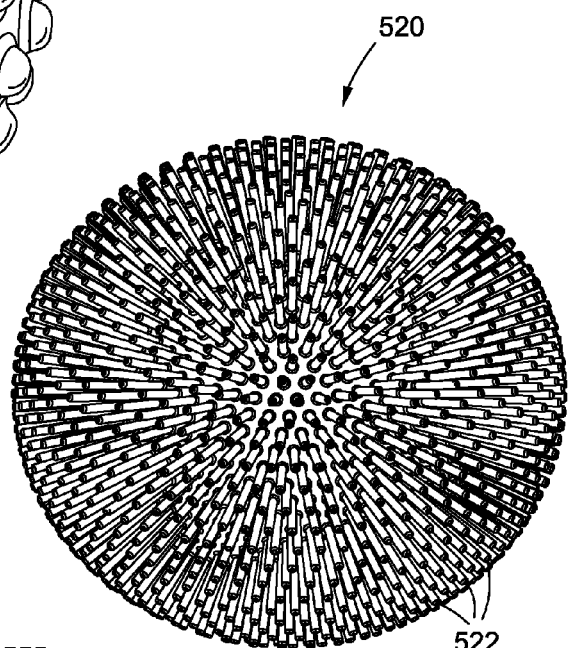

Another example of exterior stimulation features is seen in FIG. 32, where an intragastric implant 520 formed as a sphere features a multitude of small flagella or quill-like extensions 522 extending outward therefrom. As shown, a plurality of extensions 522 may be equally spaced apart. In one embodiment, the extensions 522 may be of equal heights and diameters, or they may be configured to have different heights and/or diameters. In one embodiment, the extensions 522 may be extremely flexible and may bend when a pressure is exerted on them from the inner stomach wall of the patient. Alternatively, the extensions 522 may be stiffer and might not bend as much when a pressure is exerted on them from the inner stomach wall of the patient. In another embodiment, some of the extensions 522 may have a first flexibility while some of the extensions may have a second flexibility.

Figure 33:
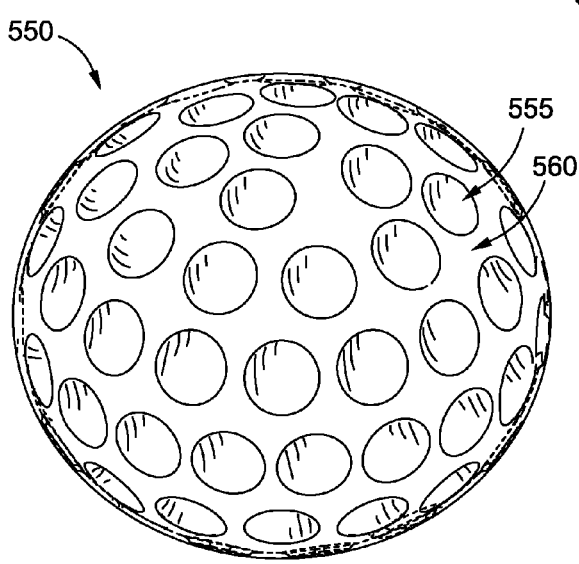

FIG. 33 illustrates another example of uneven surface features on an intragastric implant 550. As shown, the intragastric implant 550 is a substantially spherical object with recesses or dimples 555 extending inward from the surface of the intragastric implant 550. In one embodiment, the intragastric implant 550 may be considered to have a surface comprised of recesses 555 and flat portions 560. As shown, a plurality of recesses 555 may be equally spaced apart on the outer surface. As shown, recesses 555 do not contact each other, and may be of equal heights and diameters. In addition to being depressed, the recesses 555 may employ a thinner wall. For example, if the flat portions 560 have a wall thickness of 20 millimeters, the recesses 555 may have a wall thickness of 10 millimeters. With a thinner wall, the recesses 555 may be more susceptible to larger strains. The intragastric implant 550 is effectively triggered in the patient's stomach by stomach contractions. These stomach contractions increase the pressure in the intragastric implant 550. If one recess 555 is not in contact with the stomach wall, it will deform outward until it comes into contact with the stomach wall.

It should be noted that the embodiments shown in FIGS. 31-33 rotate freely within the stomach, and that the bumps 512, quill-like extensions 522, or recesses 555 may be provided in a non-uniform distribution so as to take advantage of the benefits of the rotational variation described above. That is, a regular array of such exterior features may stimulate the stomach wall more than a smooth surface, but also providing a non-uniform distribution will create different sensations on a constantly changing basis.

In accordance with various embodiments, the intragastric obesity treatment implants disclosed herein may be advantageously configured to utilize naturally occurring and/or transient stomach contractions to trigger a sustained change in the implant, which results in a physiological response that may in turn result in weight loss. It should be noted that the feeling of satiety induced by the stimulation mechanisms disclosed herein is often aligned with feeding, such that the patient may begin to associate the two events—eating a meal and feeling sated.

Various materials may be used to construct the components disclosed in the various embodiments herein, for example, rubbers, fluorosilicones, fluoroelastomers, thermoplastic elastomers, thermoplastics, thermosets, metals, glass, or any combinations thereof. It should also be understood that certain components may be removed or added without departing from the scope of the present invention.

The implantable devices described herein will be subjected to clinical testing in humans. The devices are intended to treat obesity, which is variously defined by different medical authorities. In general, the terms "overweight" and "obese" are labels for ranges of weight that are greater than what is generally considered healthy for a given height. The terms also identify ranges of weight that have been shown to increase the likelihood of certain diseases and other health problems. Applicants propose implanting the devices as described herein into a clinical survey group of obese patients in order to monitor weight loss.

In one study, clinical studies will utilize a dual-balloon implant similar to the intragastric obesity treatment implant 100 described above with reference to FIGS. 18-19 and in conjunction with the following parameters.

Materials:

Silicone materials used include 3206 silicone for any shells, inflatable structures, or otherwise flexible hollow structures. Any fill valves will be made from 4850 silicone with 6% $BaSO_4$. Tubular structures or other flexible conduits will be made from silicone rubber as defined by the Food and Drug Administration (FDA) in the Code of Federal Regulations (CFR) Title 21 Section 177.2600.

Dimensions:

Total length of implant 100—between 10-26 cm (4-10 inch), preferably 12 cm (4.75 inch)

Diameters of upper and lower reservoirs reservoir 110, 112—5-13 cm (2-5 inch), preferably 5 cm (2 inch)

OD of connecting tether 114—3-13 mm (0.125-0.50 inch), preferably 9 mm (0.36 inch)

Purposes:

the devices are for human implant, the devices are intended to occupy gastric space while also applying intermittent pressure to various and continually changing areas of the stomach;

the devices are intended to stimulate feelings of satiety, thereby functioning as a treatment for obesity.

General Implant Procedures:

The device is intended to be implanted transorally via endoscope into the corpus of the stomach.

Implantation of the medical devices will occur via endoscopy.

Nasal/Respiratory administration of oxygen and isoflurane to be used during surgical procedures to maintain anesthesia as necessary.

When deployed this device will occupy space in the caudal aspect of the corpus and in portions of the rostral corpus or antrum. The device is non-fixating and will be inflated using isotonic saline. The image below is an appropriately scaled rendering of the device in its deployed state.

One exemplary implant procedure is listed below.

a. Perform preliminary endoscopy on the patient to examine the GI tract and determine if there are any anatomical anomalies which may affect the procedure and/or outcome of the study.

b. Insert and introducer into the over-tube.

c. Insert a gastroscope through the introducer inlet until the flexible portion of the gastroscope is fully exited the distal end of the introducer.

d. Leading under endoscopic vision, gently navigate the gastroscope, followed by the introducer/over-tube, into the stomach.

e. Remove gastroscope and introducer while keeping the over-tube in place.

f. OPTIONAL: Place the insufflation cap on the over-tubes inlet, insert the gastroscope, and navigate back to the stomach cavity.

g. OPTIONAL: Insufflate the stomach with air/inert gas to provide greater endoscopic visual working volume.

h. Fold the Dual-Balloon implant (similar to a balloon catheter) and insert the lubricated implant into the over-tube, with inflation catheter following.

i. Under endoscopic vision, push the Dual-Balloon implant down the over-tube with gastroscope until visual confirmation of deployment of the device into the stomach can be determined.

j. Remove the guide-wire from the inflation catheter is used.

k. Inflate the implant using a standard BioEnterics Intragastric Balloon System ("BIB System") Fill kit. NOTE: Table 2 illustrates the relative inflation volumes associated with the various scaled implants appropriately selected at the time of implant.

l. Using 50-60 cc increments, inflate the volume to the desired fill volume.

m. Remove the inflation catheter via over-tube.

n. Inspect the Dual-Balloon implant under endoscopic vision for valve leakage, and any other potential anomalies. Record all observations.

o. Remove the gastroscope from over-tube.

p. Remove the over-tube from the patient.

TABLE 2

Dual-Balloon Device Selection, Scaling, and exemplary Fill Volumes Fill volume range of 400-700 mL (this is the fill range of a standard BioEnterics Intragastric Balloon System ("BIB System") per the directions for use), with a nominal fill of 550 mL.

| Device | Scaling – (% Relative to clinical BIB) | Max. Fill (cc) |
| --- | --- | --- |
| A | 50 | 275 |
| B | 60 | 330 |
| C | 70 | 385 |

End Point Criteria:
Weight Loss
Comprehensive Metabolic Panel (CMP)
HbA1C
Lipid Panel
Tissue Samples/Response Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references may have been made to patents and printed publications in this specification. Each of the above-cited references and printed publications are individually incorporated herein by reference in their entirety.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. An intragastric obesity treatment implant, comprising:
   a first inflatable balloon configured to be disposed in a patient's stomach, wherein the first inflatable balloon is configured to be inflated with a fluid after implantation in the patient's stomach;
   a second inflatable balloon fluidly coupled to the first inflatable balloon such that the inflatable balloons have a longitudinal length that substantially spans the stomach and the second inflatable balloon is positioned adjacent the cardia, wherein the second inflatable balloon is configured to be inflated with a fluid after implantation in the patient's stomach;
   an elongated member extending between and spacing the first and second inflatable balloons, the elongated member defining a fluid passageway in communication with the first and second balloons, the elongated member including a flow restrictor that reduces the size of the passageway while allowing and regulating fluid flow between the first and the second inflatable balloons, wherein the first inflatable balloon is constructed to receive an applied peristaltic inward pressure on the first inflatable balloon that compresses the first balloon to increase the pressure of the fluid within the first inflatable balloon to a pressure that exceeds the pressure of the fluid in the second inflatable balloon to displace a portion of the fluid within the first inflatable balloon through the flow restrictor and into the second inflatable balloon, and wherein the second inflatable balloon is constructed to receive the portion of the fluid from the first inflatable balloon to expand the second inflatable balloon to exert pressure on the cardia and induce a feeling of satiety in the patient and to equalize fluid pressure in the first and second inflatable balloons, and wherein the quantity of the portion of fluid displaced is based on a difference in pressure between fluid in the first inflatable balloon and fluid in the second inflatable balloon.

2. The implant of claim 1, wherein the first inflatable balloon and the second inflatable balloon comprise a plurality of external grooves oriented along an axis connecting the two balloons and configured to allow ingested food to pass by so that the ingested food may be digested by the patient.

3. The implant of claim 2, wherein the first inflatable balloon comprises eight grooves, and wherein the second inflatable balloon comprises eight grooves.

4. The implant of claim 1, wherein the flow restrictor comprises a narrow portion connecting the first inflatable balloon and the second inflatable balloon, and further including an elastic band wrapped around the narrow portion.

5. The implant of claim 1, wherein the flow restrictor comprises a narrow portion connecting the first inflatable balloon and the second inflatable balloon, and wherein the narrow portion includes fluted wings configured to provide structural support to the narrow portion.

6. The implant of claim 1, further including a single evacuation valve that may be accessed with an aspirator to simultaneously evacuate both the first and second inflatable balloons.

7. The implant of claim 1, wherein the implant has a dog-bone shape, with identical first and second inflatable balloons defining enlarged outer ends joined by a smaller middle portion.

8. The implant of claim 1, wherein the first and second inflatable balloons each includes an inner end wall diametrically-oriented with respect to the longitudinal axis, the end walls being joined in abutting relationship to form a partition in the implant, and wherein the flow restrictor comprises fluid passageways across the partition.

9. The implant of claim 8, further including a valve positioned in the partition that permits flow from the first inflatable balloon to the second inflatable balloon but prevents reverse flow therebetween, the valve having a flow rate capacity greater than the fluid passageways of the flow restrictor.

10. The implant of claim 8, wherein the first and second inflatable balloons have a generally uniform longitudinal exterior shape.

11. The implant of claim 1, wherein the second inflatable balloon is at least three times the volume of the first inflatable balloon.

12. The implant of claim 1, wherein the combined volumes of the first and second inflatable balloons is at least about 400 ml of saline.

13. The implant of claim 1, further including a tether having a first fluid passage fluidly connecting the first and second inflatable balloons and having the constantly open flow restrictor therein.

14. The implant of claim 13, wherein the tether also has a second passage in addition to the first passage, the second passage having one-way flow valves therein at each end adjacent each of the first and second inflatable balloons that prevent fluid from traveling from the second passage into the respective first or second inflatable balloon but permit flow from the respective first or second inflatable balloon into the second passage upon a predetermined pressure differential thereacross.

15. The implant of claim 13, wherein the first fluid passage has a size that permits a maximum flow rate of about 1-20 ml/s.

16. The implant of claim 1, wherein the first and second inflatable balloons are constructed to expand and contract to equalize fluid pressure in the first and second inflatable balloons.

* * * * *